(12) United States Patent
Heinelt et al.

(10) Patent No.: US 7,863,269 B2
(45) Date of Patent: Jan. 4, 2011

(54) IMINO-IMIDAZO-PYRIDINE DERIVATIVES HAVING ANTITHROMBOTIC ACTIVITY

(75) Inventors: Uwe Heinelt, Frankfurt am Main (DE); Armin Hofmeister, Frankfurt am Main (DE); Joerg Czech, Frankfurt am Main (DE)

(73) Assignee: sanofi-aventis, Paris (FR)

( * ) Notice: Subject to any disclaimer, the term of this patent is extended or adjusted under 35 U.S.C. 154(b) by 63 days.

(21) Appl. No.: 12/364,124

(22) Filed: Feb. 2, 2009

(65) Prior Publication Data

US 2009/0192150 A1 Jul. 30, 2009

Related U.S. Application Data

(63) Continuation of application No. PCT/EP2007/006360, filed on Jul. 18, 2007.

(30) Foreign Application Priority Data

Aug. 2, 2006 (DE) ........................ 10 2006 036 023

(51) Int. Cl.
- *A61K 31/538* (2006.01)
- *A61K 31/5377* (2006.01)
- *C07D 471/04* (2006.01)
- *C07D 213/36* (2006.01)
- *C07D 323/07* (2006.01)
- *A61P 9/00* (2006.01)
- *A61P 19/02* (2006.01)

(52) U.S. Cl. ................. 514/230.5; 514/300; 514/233.2; 546/121; 546/334; 544/127; 544/105; 568/74

(58) Field of Classification Search ............. 514/230.5, 514/300, 233.2; 546/121, 334; 544/127, 544/105; 568/74
See application file for complete search history.

(56) References Cited

U.S. PATENT DOCUMENTS

| | | | |
|---|---|---|---|
| 3,790,586 A | 2/1974 | Irikura et al. | |
| 6,063,847 A | 5/2000 | Chackalamannil et al. | |
| 7,317,124 B2 | 1/2008 | Kleemann et al. | |
| 2004/0152736 A1 | 8/2004 | Chackalamannil et al. | |

FOREIGN PATENT DOCUMENTS

| | | | |
|---|---|---|---|
| DE | 2 221 796 | | 11/1972 |
| EP | 1 391 456 | | 2/2004 |
| EP | 1391451 | | 2/2004 |
| EP | 1 602 646 | | 12/2005 |
| WO | 8502843 | * | 7/1985 |
| WO | WO 03/089428 A1 | | 10/2003 |
| WO | WO 2004/078721 A1 | | 9/2004 |
| WO | WO 2005/047240 A1 | | 5/2005 |

OTHER PUBLICATIONS

Ziessel, R., et. al., Convenient and Multistep Preparation of Oligopyridines Bearing Multiple Dansyl and Nitroxide Radicals, Synthesis, (2003), vol. 14, pp. 2145-2154.
Art-Mohand, S., New and Convenient Method for Incorporation of Pentafluorosulfanyl (SF5) Substituents Into Aliphatic Organic Compounds, Organic Letters, vol. 4. No. 17, pp. 3013-3015, (2002).
Bowden, R. et. al., A New Method for the Synthesis of Aromatic Sulfurpentafluorides and Studies of the Stability of the Sulfurpentafluoride Group in Common Synthetic Transformations, Tetrahedron 2000, vol. 56 pp. 3399-3408.
Brass, S., et. al, Platelets and Proteases, Nature, vol. 413, (2001), pp. 26-27.
Cappelli, A., et. al., A Non-Peptide NK1 Receptor Agonist Showing Subpicomolar Affinity, J. Med. Chem., (2004), vol. 47, pp. 1315-1318.
Choong, I. C., et. al., Identification of Potent and Selective Small-Molecule Inhibitors of Caspase-3 Through the Use of Extended Tethering and Structure-Based Drug Design, J. Med. Chem., (2002), vol. 45, pp. 5005-5022.
Cui, J. J., et. al., Non-Covalent Thrombin Inhibitors Featuring P3-Heterocycles With P1-Bicyclic Arginine Surrogates, Bioorganic & Medicinal Chemistry Letters, vol. 12, (2002), pp. 2925-2930.
Hollenberg, et. al., International Union of Pharmacology. XXVIII. Proteinase-Activated Receptors, Pharmacological Reviews, vol. 54, No. 2, pp. 203-217, (2002).
Lebsack, A. D., et. al.,, Identification and Synthesis of [1,2,4]Triazolo[3,4-a]Phthalazine Derivatives as High-Affinity Ligands to the a28-1 Subunit of Voltage Gated Calcium Channel, Bioorganic & Medicinal Chemistry Letters, vol. 14, pp. 2463-2467, (2004).
Saito, et. al.,, Facile Synthesis of 1,2,3,4-Tetrahydroisoquinolines Through Cyclization of 0,N-Acetals. II. 1) Syn-Processes of Isoquinolinequinone Antibiotics, Chem. Pharm. Bull., vol. 37, no. 6, pp. 1493-1499, (1989).

* cited by examiner

*Primary Examiner*—D. Margaret Seaman
*Assistant Examiner*—Niloofar Rahmani
(74) *Attorney, Agent, or Firm*—Ronald G. Ort

(57) ABSTRACT

The invention relates to compounds of the formula I

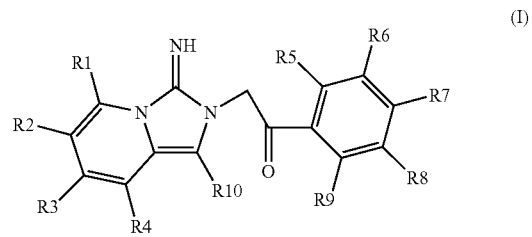

having antithrombotic activity, which in particular inhibit the protease-activated receptor 1 (PAR1), processes for their preparation and use thereof as medicaments.

10 Claims, No Drawings

IMINO-IMIDAZO-PYRIDINE DERIVATIVES HAVING ANTITHROMBOTIC ACTIVITY

The invention relates to novel compounds of the formula I having antithrombotic activity, which in particular inhibit the protease-activated receptor 1 (PAR1), processes for their preparation and use thereof as medicaments.

The protease-activated receptor 1 (PAR1) is a thrombin receptor which belongs to the class of G protein-coupled receptors (GPCR). The gene for PAR1 is on chromosome 5q13, consists of two exons and covers a region of approximately 27 kb. PAR1 is expressed, inter alia, in endothelial cells, smooth muscle cells, fibroblasts, neurons and human blood platelets. In blood platelets, PAR1 is an important receptor of signal transmission which is involved in the initiation of the aggregation of blood platelets. The activation of PARs takes place by means of the proteolytic cleavage of a part of the N terminus of the PARs, whereby a new N-terminal sequence is exposed, which then activates the receptor (Pharmacol Rev 54:203-217, 2002).

Blood clotting is a process of control of the blood flow essential for the survival of mammals. The process of clotting and the subsequent dissolution of the clot after wound healing has taken place commences after vessel damage and can be divided into four phases:
1. The phase of vascular constriction: By means of this, the blood loss in the damaged area is decreased.
2. The next phase is that of platelet activation by thrombin. The platelets aggregate at the site of the vascular wall damage and form a still loose platelet clot. The protein fibrinogen is mainly responsible for the stimulation of platelet aggregation. Platelets also bind to exposed collagen of the damaged vessel wall.
3. The initially still loose platelet aggregate is crosslinked by fibrin. If the thrombus only contains platelets and fibrin, it is a white thrombus: if red blood corpuscles are additionally present, it is a red thrombus.
4. After wound healing, the thrombus is dissolved by the action of the protein plasmin.

Two alternative pathways lead to the formation of a fibrin clot, the intrinsic pathway and the extrinsic pathway. These pathways are initiated by different mechanisms, but in a later phase they converge to give a common stretch of pathway of the clotting cascade. The formation of a red thrombus or of a clot on the bottom of a vascular wall abnormality without a wound is the result of the intrinsic pathway. Fibrin clot formation as a response to tissue damage or an injury is the result of the extrinsic pathway. Both pathways contain a relatively large number of proteins, which are known as clotting factors.

The intrinsic pathway necessitates the clotting factors VIII, IX, X, XI and XII and prekallikrein, high molecular weight kininogen, calcium ions and phospholipids from platelets. Each of these proteins leads to the activation of factor X. The intrinsic pathway is initiated when prekallikrein, high molecular weight kininogen factor XI and XII bind to a negatively charged surface. This moment is designated as the contact phase. Exposure to vessel wall collagen is the primary stimulus of the contact phase. The result of the processes of the contact phase is the conversion of prekallikrein to kallikrein, which in turn activates factor XII. Factor XIIa hydrolyzes further prekallikrein to kallikrein, so activation is the result. With increasing activation of factor XII, activation of factor XI occurs, which leads to a release of bradykinin, a vasodilator. Thus ending of the initial phase of vasoconstriction occurs. Bradykinin results from the high molecular weight kininogen. In the presence of $Ca^{2+}$ ions, factor XIa activates factor IX. Factor IX is a proenzyme, which contains vitamin K-dependent, c-carboxyglutamate (GLA) radicals. The serine protease activity becomes apparent after binding of $Ca^{2+}$ ions to these GLA radicals. A number of the serine proteases of the blood clotting cascade (factors II, VII, IX and X) contain such vitamin K-dependent GLA radicals. Factor IXa cleaves factor X and leads to activation to factor Xa. The prerequisite for the formation of factor IXa is the formation of a kinase complex from $Ca^{2+}$ ions and factors VIIIa, IXa and X on the surface of activated platelets. One of the reactions of activated platelets is the presentation of phosphatidylserine and phosphatidylinositol along the surfaces. The exposure of these phospholipids makes only the formation of the kinase complex possible. In this process, factor VIII has the function of a receptor for factors IXa and X. Factor VIII is therefore a cofactor in the clotting cascade. The activation of factor VIII with formation of factor VIIIa, the actual receptor, needs only a minimal amount of thrombin. With increase in the concentration of thrombin, factor VIIIa is finally cleaved further by thrombin and inactivated. This dual activity of the thrombin with respect to factor VIII leads to a self-limitation of kinase complex formation and thus to a containment of the blood clotting.

In the activation of human blood platelets by thrombin, PAR1 and PAR4 play a central role; the activation of these receptors in blood platelets leads to morphological changes, release of ADP and aggregation of the blood platelets (Nature 413:26-27, 2001).

Inhibitors of PAR 1 are described, for example, in European patent applications EP1391451 or EP1391452, American patent applications U.S. Pat. No. 6,063,847 and US 2004/0152736 and International application WO 03/089428.

The compounds of the formula I according to the invention are suitable for prophylactic and for therapeutic use in humans who are suffering from diseases which are accompanied by thromboses, embolisms, hypercoagulability or fibrotic changes. Examples of such diseases are thrombosis, deep vein thrombosis, pulmonary embolisms, cerebral infarct, cardiac infarct, high blood pressure, inflammatory diseases, rheumatism, asthma, glomerulonephritis or osteoporosis. The compounds of the formula I according to the invention can be employed for secondary prevention and are suitable both for acute therapy and for long-term therapy.

The invention therefore relates to a compound of the formula I

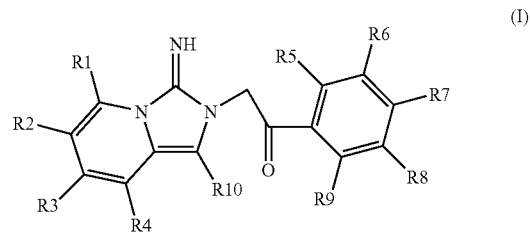

(I)

and/or all stereoisomeric or tautomeric forms of the compound of the formula I and/or mixtures of these forms in any ratio, and/or a physiologically tolerable salt of the compound of the formula I, where
R1, R2, R3 and R4 are identical or different and independently of one another are
1) —$(C_1-C_6)$-alkyl, where alkyl is unsubstituted or mono-, di- or trisubstituted independently of one another by —$(C_6-C_{14})$-aryl, —$(C_3-C_6)$-cycloalkyl, Het, halogen, —$NH_2$, —OH or methoxy, 2) —O—($C_1$-$C_8$)-alkyl, where alkyl is unsubstituted or mono-, di- or trisubstituted independently of one another by —($C_6$-$C_{14}$)-aryl, —($C_3$-$C_6$)-cycloalkyl, Het, halogen, —$NH_2$, —OH or methoxy, where —($C_6$-$C_{14}$)-aryl and Het are unsubstituted or additionally mono-, di- or trisubstituted by R15,
3) —($C_0$-$C_4$)-alkylene-C(O)—R11, where R11 is
  3)1) a hydrogen atom,
  3)2) —($C_1$-$C_6$)-alkyl,
  3)3) —($C_0$-$C_4$)-alkylene-($C_6$-$C_{14}$)-aryl,
  3)4) —($C_0$-$C_4$)-alkylene-Het or
  3)5) —($C_0$-$C_4$)-alkylene-($C_3$-$C_6$)-cycloalkyl,
4) —($C_0$-$C_4$)-alkylene-C(O)—O—R11, where R11 is as defined above,
5) —($C_0$-$C_4$)-alkylene-N(R12)-R13, where R12 and R13 are identical or different and independently of one another are
  5)1) a hydrogen atom,
  5)2) —($C_1$-$C_6$)-alkyl,
  5)3) —($C_1$-$C_3$)-fluoroalkyl,
  5)4) —($C_0$-$C_4$)-alkylene-($C_6$-$C_{14}$)-aryl,
  5)5) —($C_0$-$C_4$)-alkylene-Het or
  5)6) —($C_0$-$C_4$)-alkylene-($C_3$-$C_6$)-cycloalkyl,
6) —($C_0$-$C_4$)-alkylene-C(O)—N(R12)-R13, where R12 and R13 are identical or different and independently of one another are as defined above,
7) —($C_0$-$C_4$)-alkylene-N(R12)-C(O)—R13, where R12 and R13 are identical or different and independently of one another are as defined above,
8) —($C_1$-$C_3$)-fluoroalkyl,
9) —O—($C_1$-$C_3$)-fluoroalkyl,
10) —$SO_2$—$CH_3$,
11) —$SO_2$—$CF_3$,
12) —$NO_2$,
13) —CN,
14) —OH,
15) =O,
16) a hydrogen atom or
17) halogen,
R10 and R15 are identical or different and independently of one another are
  1) a hydrogen atom,
  2) —($C_1$-$C_4$)-alkyl,
  3) —O—($C_1$-$C_4$)-alkyl,
  4) —($C_1$-$C_3$)-fluoroalkyl,
  5) —O—($C_1$-$C_3$)-fluoroalkyl,
  6) —($C_0$-$C_4$)-alkylene-N(R16)(R17), in which R16 and R17 independently of one another are a hydrogen atom or —($C_1$-$C_6$)-alkyl,
  7) —($C_0$-$C_4$)-alkylene-($C_6$-$C_{14}$)-aryl,
  8) —($C_0$-$C_4$)-alkylene-($C_3$-$C_6$)-cycloalkyl,
  9) —($C_0$-$C_4$)-alkylene-Het,
  10) —OH,
  11) =O,
  12) —$NO_2$,
  13) —CN,
  14) halogen,
  15) —$SO_2$—($C_1$-$C_4$)-alkyl or
  16) —$SO_2$—($C_1$-$C_3$)-fluoroalkyl,
R5, R6, R7, R8 and R9 are identical or different and independently of one another are
  1) a hydrogen atom,
  2) —($C_0$-$C_4$)-alkylene-($C_6$-$C_{14}$)-aryl, where aryl is unsubstituted or mono-, di- or trisubstituted independently of one another by —($C_1$-$C_4$)-alkyl, —($C_6$-$C_{14}$)-aryl, Het, —($C_3$-$C_6$)-cycloalkyl, halogen, —$NH_2$, —OH or methoxy,
  3) —($C_0$-$C_4$)-alkylene-($C_3$-$C_6$)-cycloalkyl,
  4) —($C_0$-$C_4$)-alkylene-Het, where Het is unsubstituted or mono-, di- or trisubstituted independently of one another by —($C_1$-$C_4$)-alkyl, —($C_6$-$C_{14}$)-aryl, Het, —($C_3$-$C_6$)-cycloalkyl, —C(O)—O—R16, —C(O)—N(R16)(R17), in which R16 and R17 are as defined above, halogen, —$NH_2$, —OH or methoxy,
  5) —$SF_5$,
  6) —($C_1$-$C_6$)-alkyl, where alkyl is unsubstituted or mono-, di- or trisubstituted independently of one another by halogen, —$NH_2$, —OH or methoxy,
  7) —O—($C_1$-$C_8$)-alkyl, where alkyl is unsubstituted or mono-, di- or trisubstituted independently of one another by —($C_6$-$C_{14}$)-aryl, —($C_3$-$C_6$)-cycloalkyl, Het, halogen, —$NH_2$, —OH or methoxy,
  8) —($C_0$-$C_4$)-alkylene-C(O)—R11, where R11 is as defined above,
  9) —($C_0$-$C_4$)-alkylene-C(O)—O—R11, where R11 is as defined above,
  10) —($C_0$-$C_4$)-alkylene-N(R12)-R13, where R12 and R13 are identical or different and independently of one another are as defined above,
  11) —($C_0$-$C_4$)-alkylene-C(O)—N(R12)-R13, where R12 and R13 are identical or different and independently of one another are as defined above,
  12) —($C_0$-$C_4$)-alkylene-N(R12)-C(O)—R13, where R12 and R13 are identical or different and independently of one another are as defined above,
  13) —($C_1$-$C_3$)-fluoroalkyl,
  14) —O—($C_1$-$C_3$)-fluoroalkyl,
  15) —$SO_2$—$CH_3$,
  16) —$SO_2$—$CF_3$,
  17) —$NO_2$,
  18) —CN,
  19) —OH or
  20) halogen, or
R5 and R6, R6 and R7, R7 and R8 or R8 and R9, together with the ring atoms to which they are bonded, form a four- to eight-membered heterocycle which, together with the phenyl ring to which the heterocycle is fused, forms a bicyclic system, where the heterocyclic moiety is unsubstituted or mono-, di- or trisubstituted independently of one another by —($C_1$-$C_4$)-alkyl, —($C_6$-$C_{14}$)-aryl, —($C_3$-$C_6$)-cycloalkyl, halogen, —$NH_2$, —OH or methoxy.

2) The invention further relates to a compound of the formula I and/or all stereoisomeric or tautomeric forms of the compound of the formula I and/or mixtures of these forms in any ratio, and/or a physiologically tolerable salt of the compound of the formula I, where
R1, R2, R3 and R4 are identical or different and independently of one another are
  1) —($C_1$-$C_6$)-alkyl, where alkyl is unsubstituted or mono-, di- or trisubstituted independently of one another by —($C_3$-$C_6$)-cycloalkyl, halogen, —$NH_2$, —OH, methoxy, —($C_6$-$C_{14}$)-aryl, or Het,
    where aryl is selected from the group consisting of phenyl, naphthyl, anthryl and fluorenyl and in which aryl is unsubstituted or mono-, di- or trisubstituted by R15,
    where Het is selected from the group consisting of acridinyl, azepinyl, azetidinyl, aziridinyl, benzimidazolyl, benzofuranyl, benzothiofuranyl, benzothiophenyl, benzoxazolyl, benzothiazolyl, benzotriazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2, 3-b]tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolidinyl, thiazolinyl, thiazolyl, thienyl, thienoimidazolyl, thienooxazolyl, thienopyrrolyl, thienopyridinyl, thienothiazolyl, thienothiophenyl, thiomorpholinyl, triazinyl, 1,2,3-triazolyl, 1,2,4-triazolyl, 1,2,5-triazolyl, 1,3,4-triazolyl and xanthenyl and in which Het is unsubstituted or additionally mono-, di- or trisubstituted by R15, 2) —O—($C_1$-$C_6$)-alkyl, where alkyl is unsubstituted or mono-, di- or trisubstituted independently of one another by —($C_6$-$C_{14}$)-aryl, —($C_3$-$C_6$)-cycloalkyl, Het, halogen, —$NH_2$, —OH or methoxy, where Het and aryl are as defined above, 3) —($C_0$-$C_4$)-alkylene-C(O)—R11, where R11 is
   3)1) a hydrogen atom,
   3)2) —($C_1$-$C_6$)-alkyl,
   3)3) —($C_0$-$C_4$)-alkylene-($C_6$-$C_{14}$)-aryl, where aryl is as defined above,
   3)4) —($C_0$-$C_4$)-alkylene-Het, where Het is as defined above, or
   3)5) —($C_0$-$C_4$)-alkylene-($C_3$-$C_6$)-cycloalkyl, 4) —($C_0$-$C_4$)-alkylene-C(O)—O—R11, where R11 is as defined above, 5) —($C_0$-$C_4$)-alkylene-N(R12)-R13, where R12 and R13 are identical or different and independently of one another are
   5)1) a hydrogen atom,
   5)2) —($C_1$-$C_6$)-alkyl,
   5)3) —($C_1$-$C_3$)-fluoroalkyl,
   5)4) —($C_0$-$C_4$)-alkylene-($C_6$-$C_{14}$)-aryl, where aryl is as defined above,
   5)5) —($C_0$-$C_4$)-alkylene-Het, where Het is as defined above, or
   5)6) —($C_0$-$C_4$)-alkylene-($C_3$-$C_6$)-cycloalkyl, 6) —($C_0$-$C_4$)-alkylene-C(O)—N(R12)-R13, where R12 and R13 are identical or different and independently of one another are as defined above, 7) —($C_0$-$C_4$)-alkylene-N(R12)-C(O)—R13, where R12 and R13 are identical or different and independently of one another are as defined above, 8) —($C_1$-$C_3$)-fluoroalkyl,
9) —O—($C_1$-$C_3$)-fluoroalkyl,
10) —$SO_2$—$CH_3$,
11) —$SO_2$—$CF_3$,
12) —$NO_2$,
13) —CN,
14) —OH,
15) =O,
16) a hydrogen atom or
17) halogen, R10 and R15 are identical or different and independently of one another are
1) a hydrogen atom,
2) —($C_1$-$C_4$)-alkyl,
3) —O—($C_1$-$C_4$)-alkyl,
4) —($C_1$-$C_3$)-fluoroalkyl,
5) —O—($C_1$-$C_3$)-fluoroalkyl,
6) —($C_0$-$C_4$)-alkylene-N(R16)(R17), in which R16 and R17 independently of one another are a hydrogen atom or —($C_1$-$C_6$)-alkyl,
7) —($C_0$-$C_4$)-alkylene-($C_6$-$C_{14}$)-aryl, where aryl is as defined above,
8) —($C_0$-$C_4$)-alkylene-($C_3$-$C_6$)-cycloalkyl,
9) —($C_0$-$C_4$)-alkylene-Het, where Het is as defined above,
10) —OH,
11) =O,
12) —$NO_2$,
13) —CN,
14) halogen,
15) —$SO_2$—($C_1$-$C_4$)-alkyl or
16) —$SO_2$—($C_1$-$C_3$)-fluoroalkyl, R5, R6, R7, R8 and R9 are identical or different and independently of one another are
1) a hydrogen atom,
2) —($C_0$-$C_4$)-alkylene-($C_6$-$C_{14}$)-aryl, where aryl is unsubstituted or mono-, di- or trisubstituted independently of one another by —($C_1$-$C_4$)-alkyl, —($C_6$-$C_{14}$)-aryl, Het, —($C_3$-$C_6$)-cycloalkyl, halogen, —$NH_2$, —OH or methoxy, where aryl and Het are as defined above,
3) —($C_0$-$C_4$)-alkylene-($C_3$-$C_6$)-cycloalkyl,
4) —($C_0$-$C_4$)-alkylene-Het, where Het is unsubstituted or mono-, di- or trisubstituted independently of one another by —($C_1$-$C_4$)-alkyl, —($C_6$-$C_{14}$)-aryl, Het, —($C_3$-$C_6$)-cycloalkyl, —C(O)—O—R16, —C(O)—N(R16)(R17), in which R16 and R17 are as defined above, halogen, —$NH_2$, —OH or methoxy, where aryl and Het are as defined above,
5) —$SF_5$,
6) —($C_1$-$C_6$)-alkyl, where alkyl is unsubstituted or mono-, di- or trisubstituted independently of one another by halogen, —$NH_2$, —OH or methoxy,
7) —O—($C_1$-$C_8$)-alkyl, where alkyl is unsubstituted or mono-, di- or trisubstituted independently of one another by —($C_6$-$C_{14}$)-aryl, —($C_3$-$C_6$)-cycloalkyl, Het, halogen, —$NH_2$, —OH or methoxy, where aryl and Het are as defined above,
8) —($C_0$-$C_4$)-alkylene-C(O)—R11, where R11 is as defined above,
9) —($C_0$-$C_4$)-alkylene-C(O)—O—R11, where R11 is as defined above,
10) —($C_0$-$C_4$)-alkylene-N(R12)-R13, where R12 and R13 are identical or different and independently of one another are as defined above,
11) —($C_0$-$C_4$)-alkylene-C(O)—N(R12)-R13, where R12 and R13 are identical or different and independently of one another are as defined above,
12) —($C_0$-$C_4$)-alkylene-N(R12)-C(O)—R13, where R12 and R13 are identical or different and independently of one another are as defined above,
13) —($C_1$-$C_3$)-fluoroalkyl,
14) —O—($C_1$-$C_3$)-fluoroalkyl,
15) —$SO_2$—$CH_3$,
16) —$SO_2$—$CF_3$, 17) —NO₂,
18) —CN,
19) —OH or
20) halogen, or R5 and R6, R6 and R7, R7 and R8 or R8 and R9, together with the ring atoms to which they are bonded, form a four- to eight-membered heterocycle which, together with the phenyl ring to which the heterocycle is fused, forms a bicyclic system selected from the group consisting of benzimidazole, benzisothiazole, benzisoxazole, benzo[1,3]dioxole, benzofuran, benzothiazole, benzisoxazole, benzothiofuran, benzothiophene, benzo[1,3]oxathiole, benzoxazole, benzothiazole, benzotriazole, quinazoline, quinazolone, quinoline, 4H-quinolizine, quinoxaline, chroman, chromene, cinnoline, 2,3-dihydrobenzo[1,4]dioxin, 2,3-dihydrobenzofuranyl, 1,3-dihydroisobenzofuran, 3,4-dihydro-2H-benzo[1,4]oxazine, 2,3-dihydrobenzooxazole, 2,3-dihydrobenzothiazole, 1,3-dihydrobenzo[c]thiophene, 2,3-dihydrobenzo[b]thiophene, indazole, indole, indoline, isobenzofuran, isoquinoline, isochroman, isoindazole, isoindole, isoindoline, 7-oxabicyclo[4.2.0]octa-1,3,5-triene, phthalazine, 2,3,4,5-tetrahydro-1H-benzo[b]azepine, 6,7,8,9-tetrahydro-5-oxa-9-azabenzocycloheptene, 3,4,5,6-tetrahydro-2H-benzo[b][1,4]oxazozine, tetrahydroquinoline, 1,2,3,4-tetrahydroquinoxaline or tetrahydroisoquinoline, where the heterocyclic moiety is unsubstituted or mono-, di- or trisubstituted independently of one another by —(C₁-C₄)-alkyl, —(C₆-C₁₄)-aryl, —(C₃-C₆)-cycloalkyl, halogen, —NH₂, —OH or methoxy.

3) The invention further relates to a compound of the formula I and/or all stereoisomeric or tautomeric forms of the compound of the formula I and/or mixtures of these forms in any ratio, and/or a physiologically tolerable salt of the compound of the formula I, where R1, R2, R3 and R4 are identical or different and independently of one another are
  1) a hydrogen atom,
  2) —(C₁-C₄)-alkyl,
  3) —O—(C₁-C₄)-alkyl,
  4) —(C₀-C₄)-alkylene-C(O)—N(R12)-R13, where R12 and R13 are identical or different and independently of one another are a hydrogen atom or —(C₁-C₄)-alkyl,
  5) —(C₁-C₃)-fluoroalkyl,
  6) —(C₀-C₄)-alkylene-C(O)—O—(C₁-C₄)-alkyl or
  7) =O,
  8) halogen, R10 is 1) a hydrogen atom,
  2) —(C₁-C₄)-alkyl,
  3) —(C₀-C₄)-alkylene-(C₃-C₆)-cycloalkyl or
  4) —(C₀-C₄)-alkylenephenyl, R5, R6, R7, R8 and R9 are identical or different and independently of one another are
  1) a hydrogen atom,
  2) —(C₁-C₃)-fluoroalkyl,
  3) halogen,
  4) —O—(C₁-C₄)-alkyl,
  5) —OH,
  6) —(C₁-C₄)-alkyl,
  7) —SF₅,
  8) —(C₀-C₄)-alkylene-NH—C(O)—(C₁-C₃)-fluoroalkyl,
  9) —(C₀-C₄)-alkylene-N(R12)-R13, where R12 and R13 are identical or different and independently of one another are a hydrogen atom or —(C₁-C₄)-alkyl, or
  10) —(C₀-C₄)-alkylene-Het, where Het is selected from the group consisting of morpholinyl or pyrrolidinyl and is unsubstituted or mono- or di-substituted independently of one another by —(C₁-C₄)-alkyl, =O or —NH₂, or R5 and R6, R6 and R7, R7 and R8 or R8 and R9, together with the ring atoms to which they are bonded, form a four- to eight-membered heterocycle which, together with the phenyl ring to which the heterocycle is fused, forms a bicyclic system selected from the group consisting of 2,3-dihydrobenzo[1,4]dioxin, benzo[1,3]dioxole, 3,4-dihydro-2H-benzo[1,4]oxazine, 2,3,4,5-tetrahydro-1H-benzo[b]azepine, tetrahydroquinoline, tetrahydroisoquinoline, 1,2,3,4-tetrahydroquinoxaline or 6,7,8,9-tetrahydro-5-oxa-9-azabenzocycloheptene, where the heterocyclic moiety is unsubstituted or mono- or disubstituted by —(C₁-C₄)-alkyl or halogen.

The invention further relates to compounds of the formula I from the group consisting of 1-(3,5-di-tert-butyl-4-hydroxyphenyl)-2-(3-iminoimidazo[1,5-a]pyridin-2-yl)ethanone as the trifluoroacetic acid salt, 2-(3-iminoimidazo[1,5-a]pyridin-2-yl)-1-(3-pentafluorosulfanylphenyl)ethanone as the trifluoroacetic acid salt, 2-(1-cyclopropyl-3-iminoimidazo[1,5-a]pyridin-2-yl)-1-(3,5-di-tert-butyl-4-hydroxyphenyl)ethanone as the trifluoroacetic acid salt, 1-(3,5-di-tert-butyl-4-hydroxyphenyl)-2-(3-imino-1-phenylimidazo[1,5-a]pyridin-2-yl)ethanone as the trifluoroacetic acid salt, 1-(3,5-di-tert-butyl-4-hydroxyphenyl)-2-(3-imino-8-methylimidazo[1,5-a]pyridin-2-yl)ethanone as the trifluoroacetic acid salt, 1-(3,5-di-tert-butyl-4-hydroxyphenyl)-2-(3-imino-8-methylimidazo[1,5-a]pyridin-2-yl)ethanone as the hydrobromide salt, 1-(3,5-di-tert-butyl-4-hydroxyphenyl)-2-(3-imino-7-trifluoromethylimidazo[1,5-a]pyridin-2-yl)ethanone as the trifluoroacetic acid salt, 1-(3,5-di-tert-butyl-4-hydroxyphenyl)-2-(3-imino-7-trifluoromethylimidazo[1,5-a]pyridin-2-yl)ethanone as the hydrobromide salt, methyl 2-[2-(3,5-di-tert-butyl-4-hydroxyphenyl)-2-oxoethyl]-3-imino-2,3-dihydroimidazo[1,5-a]pyridine-6-carboxylate as the trifluoroacetic acid salt, methyl 2-[2-(3-tert-butyl-4-methoxy-5-morpholin-4-ylphenyl)-2-oxoethyl]-3-imino-2,3-dihydroimidazo[1,5-a]pyridine-6-carboxylate as the trifluoroacetic acid salt, 1-(3-tert-butyl-4-methoxy-5-morpholin-4-ylphenyl)-2-(3-iminoimidazo[1,5-a]pyridin-2-yl)ethanone as the trifluoroacetic acid salt, 1-(3-tert-butyl-4-methoxy-5-morpholin-4-ylphenyl)-2-(3-imino-8-methylimidazo[1,5-a]pyridin-2-yl)ethanone as the trifluoroacetic acid salt, 1-(3-dimethylamino-5-pentafluorosulfanylphenyl)-2-(3-iminoimidazo[1,5-a]pyridin-2-yl)ethanone as the trifluoroacetic acid salt, 2-[2-(8-tert-butyl-4-methyl-3,4-dihydro-2H-benzo[1,4]oxazin-6-yl)-2-oxoethyl]-7-ethoxy-3-imino-2,3-dihydroimidazo[1,5-a]pyridine-6-carboxylic acid methylamide as the trifluoroacetic acid salt, 2-[2-(3-tert-butyl-4-methoxy-5-morpholin-4-ylphenyl)-2-oxoethyl]-7-chloro-3-imino-2,3-dihydroimidazo[1,5-a]pyridine-6-carboxylic acid methylamide as the trifluoroacetic acid salt, 2,2,2-trifluoro-N-{3-[2-(3-iminoimidazo[1,5-a]pyridin-2-yl)acetyl]-5-pentafluorosulfanylphenyl}acetamide as the trifluoroacetic acid salt, 1-(3-bromo-4-methoxy-5-trifluoromethylphenyl)-2-(3-iminoimidazo[1,5-a]pyridin-2-yl)-ethanone as the trifluoroacetic acid salt, 2-(3-iminoimidazo[1,5-a]pyridin-2-yl)-1-(4-methoxy-3-morpholin-4-yl-5-trifluoromethylphenyl)ethanone as the trifluoroacetic acid salt, 6-ethoxy-3-imino-2-[2-(3-methylamino-5-pentafluorosulfanylphenyl)-2-oxoethyl]-2,3-dihydro-1H-imidazo[1,5-a]pyridin-5-one as the trifluoroacetic acid salt, 2-[2-(3-tert-butyl-4-methoxy-5-morpholin-4-ylphenyl)-2-oxoethyl]-6-ethoxy-3-imino-2,3-dihydro-1H-imidazo[1,5-a]pyridin-5-one as the trifluoroacetic acid salt, 2-[2-(3-tert-butyl-4-methoxy-5-morpholin-4-ylphenyl)-2-oxoethyl]-7-ethoxy-3-imino-2,3-dihydroimidazo[1,5-a]pyridine-6-carboxylic acid methylamide as the trifluoroacetic acid salt or ethyl 2-[2-(3-tert-butyl-4-methoxy-5-morpholin-4-yl phenyl)-2-oxoethyl]-3-imino-5-methoxy-2,3-dihydroimidazo[1,5-a]pyridine-7-carboxylate as the trifluoroacetic acid salt.

The term "$(C_1-C_4)$-alkyl" or "$(C_1-C_6)$-alkyl" is understood as meaning hydrocarbon radicals whose carbon chain is straight-chain or branched and contains 1 to 4 carbon atoms or 1 to 6 carbon atoms, for example methyl, ethyl, propyl, isopropyl, butyl, isobutyl, sec-butyl, tertiary-butyl, pentyl, isopentyl, neopentyl, 1-ethylpropyl, hexyl, 2,3-dimethylbutyl or neohexyl.

The term "—$(C_0-C_4)$-alkylene" is understood as meaning hydrocarbon radicals whose carbon chain is straight-chain or branched and contains 1 to 4 carbon atoms, for example methylene, ethylene, 1-methylmethylene, propylene, 1-methylethylene, butylene, 1-propylmethylene, 1-ethyl-1-methylmethylene, 1,2-dimethylethylene, 1,1-dimethylmethylene, 1-ethyl ethylene, 1-methylpropylene, 2-methylpropylene. "—$C_0$-alkylene" is a covalent bond.

The term "—O—$(C_1-C_8)$-alkyl" is understood as meaning alkoxy radicals whose carbon chain is straight-chain or branched and contains 1 to 8 carbon atoms, for example methoxy, ethoxy, propoxy, isopropoxy, butoxy, isobutoxy or tertiary-butoxy.

The term "$(C_3-C_6)$-cycloalkyl" is understood as meaning radicals such as compounds which are derived from 3- to 6-membered monocycles such as cyclopropane, cyclobutane, cyclopentane or cyclohexane.

The term "—$(C_6-C_{14})$-aryl" is understood as meaning aromatic carbon radicals having 6 to 14 carbon atoms in the ring. —$(C_6-C_{14})$-Aryl radicals are, for example, phenyl, naphthyl, for example 1-naphthyl, 2-naphthyl, anthryl or fluorenyl. Naphthyl radicals and in particular phenyl radicals are preferred aryl radicals.

The term "Het" is understood as meaning ring systems having 4 to 15 carbon atoms, which are present in one, two or three ring systems bonded to one another and which each, depending on ring size, contain one, two, three or four identical or different heteroatoms from the group consisting of oxygen, nitrogen or sulfur. Examples of these ring systems are the radicals acridinyl, azepinyl, azetidinyl, aziridinyl, benzimidazolyl, benzofuranyl, benzothiofuranyl, benzothiophenyl, benzoxazolyl, benzothiazolyl, benzotriazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]tetrahydrofuranyl, dihydrofuranyl, dioxolyl, dioxanyl, 2H,6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isoquinolinyl, isochromanyl, isoindazolyl, isoindolinyl, isoindolyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxothiolanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolidinyl, thiazolinyl, thiazolyl, thienyl, thienoimidazolyl, thienooxazolyl, thienopyrrolyl, thienopyridinyl, thienothiazolyl, thienothiophenyl, thiomorpholinyl, triazinyl, 1,2,3-triazolyl, 1,2,4-triazolyl, 1,2,5-triazolyl, 1,3,4-triazolyl or xanthenyl.

R5 and R6, R6 and R7, R7 and R8 or R8 and R9, together with the ring atoms to which they are bonded, form a four- to eight-membered heterocycle which, together with the phenyl ring to which the heterocycle is fused, forms a bicyclic system compounds are understood which consist of two ring systems bonded to one another, in which one ring is a phenyl radical and the other ring forms a partially saturated or aromatic ring system which, depending on ring size, contains one, two or three identical or different heteroatoms from the group consisting of oxygen, nitrogen or sulfur. Examples of these ring systems are radicals such as benzimidazole, benzisothiazole, benzisoxazole, benzo[1,3]dioxole, benzofuranyl, benzothiazole, benzisoxazole, benzothiofuran, benzothiophene, benzo[1,3]oxathiole, benzoxazole, benzothiazole, benzotriazole, quinazoline, quinazolone, quinoline, 4H-quinolizine, quinoxaline, chroman, chromene, cinnoline, 2,3-dihydrobenzo[1,4]dioxin, 2,3-dihydrobenzofuranyl, 1,3-dihydroisobenzofuran, 3,4-dihydro-2H-benzo[1,4]oxazine, 2,3-dihydrobenzooxazole, 2,3-dihydrobenzothiazole, 1,3-dihydrobenzo[c]thiophene, 2,3-dihydrobenzo[b]thiophene, indazole, indole, indoline, isobenzofuran, isoquinoline, isochroman, isoindazole, isoindole, isoindoline, 7-oxabicyclo[4.2.0]octa-1,3,5-triene, phthalazine, 2,3,4,5-tetrahydro-1H-benzo[b]azepine, 6,7,8,9-tetrahydro-5-oxa-9-azabenzocycloheptene, 3,4,5,6-tetrahydro-2H-benzo[b][1,4]oxazozine, tetrahydroquinoline, 1,2,3,4-tetrahydroquinoxaline or tetrahydroisoquinoline.

The term "—$(C_1-C_3)$-fluoroalkyl" is understood as meaning a partially or completely fluorinated alkyl radical, which is derived, for example, from the following radicals —$CF_3$, —$CHF_2$, —$CH_2F$, —$CHF—CF_3$, —$CHF—CHF_2$, —$CHF—CH_2F$, —$CH_2—CF_3$, —$CH_2—CHF_2$, —$CH_2—CH_2F$, —$CF_2—CF_3$, —$CF_2—CHF_2$, —$CF_2—CH_2F$, —$CH_2—CHF—CF_3$, —$CH_2—CHF—CHF_2$, —$CH_2—CHF—CH_2F$, —$CH_2—CH_2—CF_3$, —$CH_2—CH_2—CHF_2$, —$CH_2—CH_2—CH_2F$, —$CH_2—CF_2—CF_3$, —$CH_2—CF_2—CHF_2$, —$CH_2—CF_2—CH_2F$, —$CHF—CHF—CF_3$, —$CHF—CHF—CHF_2$, —$CHF—CHF—CH_2F$, —$CHF—CH_2—CF_3$, —$CHF—CH_2—CHF_2$, —$CHF—CH_2—CH_2F$, —$CHF—CF_2—CF_3$, —$CHF—CF_2—CHF_2$, —$CHF—CF_2—CH_2F$, —$CF_2—CHF—CF_3$, —$CF_2—CHF—CHF_2$, —$CF_2—CHF—CH_2F$, —$CF_2—CH_2—CF_3$, —$CF_2—CH_2—CHF_2$, —$CF_2—CH_2—CH_2F$, —$CF_2—CF_2—CF_3$, —$CF_2—CF_2—CHF_2$ or —$CF_2—CF_2—CH_2F$.

The term "halogen" is understood as meaning fluorine, chlorine, bromine or iodine; fluorine, chlorine or bromine is preferred, in particular fluorine or chlorine.

The term "=O" is understood as meaning radicals such as carbonyl (—C(O)—) or nitroso (—N=O).

Functional groups of the intermediates used, for example amino or carboxyl groups in the compound of the formula I, can be masked here by suitable protective groups. Suitable protective groups for amino functions are, for example, the t-butoxycarbonyl, the benzyloxycarbonyl or the phthalolyl group and the trityl or tosyl protective group. Suitable protective groups for the carboxyl function are, for example, alkyl, aryl or arylalkyl esters. Protective groups can be introduced and removed by techniques which are well-known or described here (see Greene, T. W., Wuts, P. G. M., *Protective Groups in Organic Synthesis* (1999), 3rd Ed., Wiley-Interscience). The term protective group can also include appropriate polymer-bound protective groups.

The compounds according to the invention can be prepared by well-known processes or processes which are described here.

Also included are possible tautomeric forms of the structures indicated, such as, for example, of the formula III/IIIt or I/It (when R1 in formula I is, for example, OH):

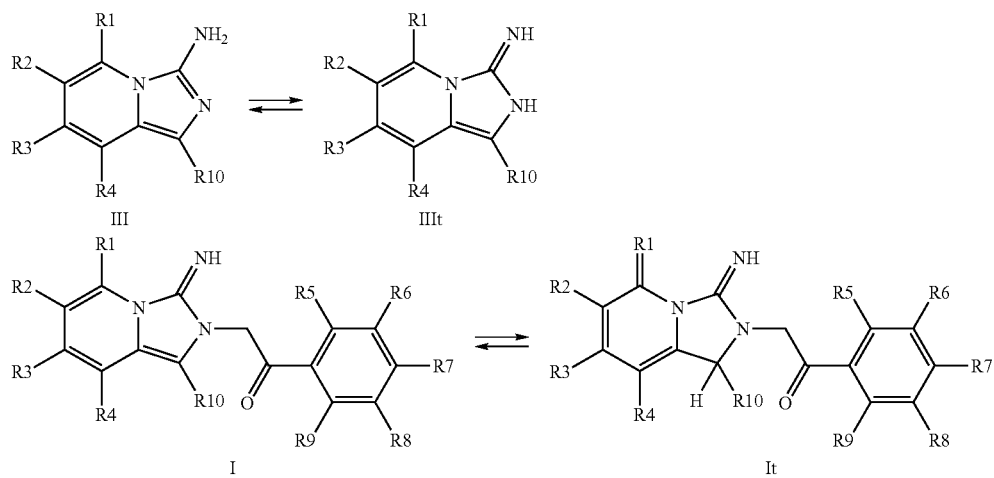

The invention further relates to a process for the preparation of the compound of the formula I and/or a stereoisomeric form of the compound of the formula I and/or a physiologically tolerable salt of the compound of the formula I, which comprises a) reacting a compound of the formula II

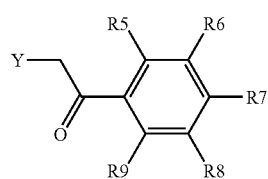

where the radicals R5, R6, R7, R8 and R9 are as defined in formula I and Y is chloride, bromide, mesylate or tosylate, with a compound of the formula III

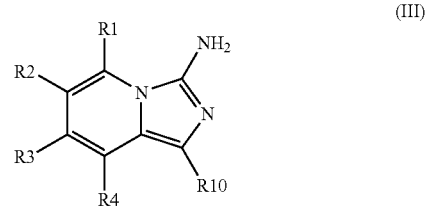

in the presence of a base and of a solvent to give a compound of the formula I, or b) reacting a compound of the formula VII

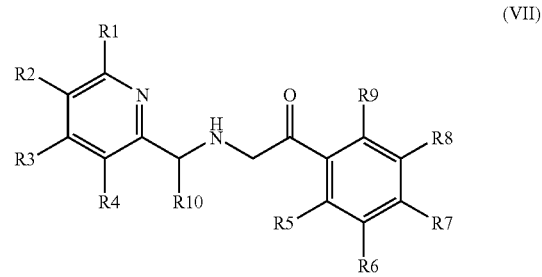

where the radicals R1 to R10 are as defined in formula I, with a compound Z-CN, where Z is tosylate or bromide, in the presence of a base to give a compound of the formula I, or c) either isolating the compound of the formula I prepared according to process a) or b) in free form or releasing it from physiologically intolerable salts or, in the case of the presence of acidic or basic groups, converting it to physiologically tolerable salts, or d) separating a compound of the formula I prepared according to process a) or b), or a suitable precursor of the formula I, which on account of its chemical structure occurs in enantiomeric or diastereomeric forms, by salt formation with enantiomerically pure acids or bases, chromatography on chiral stationary phases or derivatization by means of chiral enantiomerically pure compounds such as amino acids, separation of the diastereomers thus obtained, and cleavage of the chiral auxiliary groups into the pure enantiomers or diastereomers.

The invention further relates to a process for the preparation of the compound of the formula I according to scheme 1.

Scheme 1:

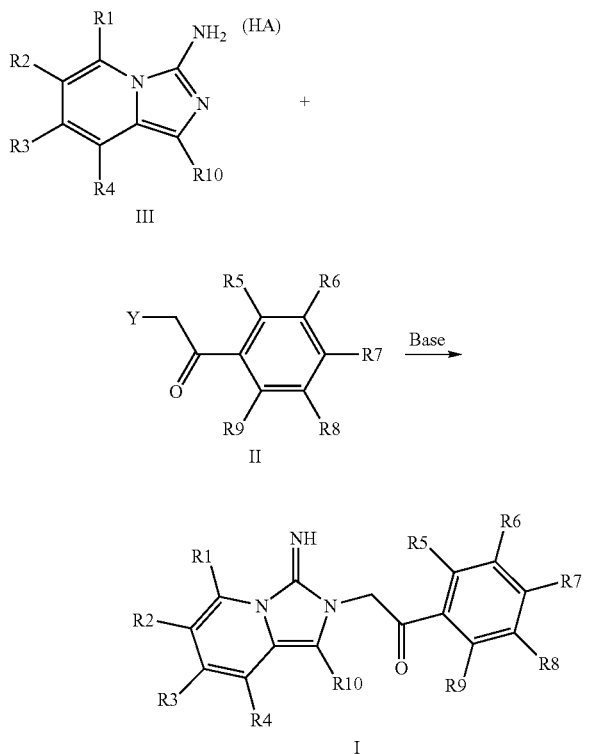

Scheme 2:

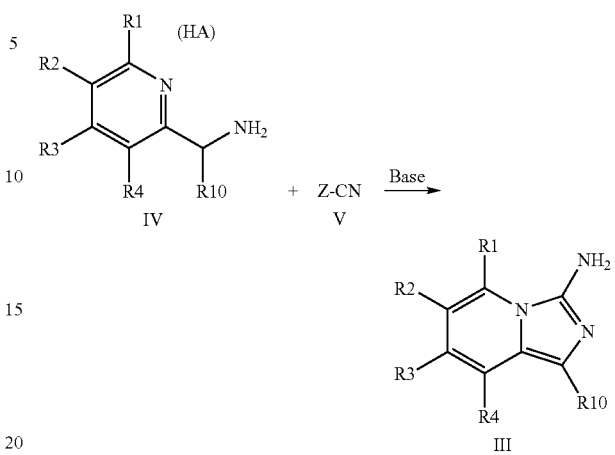

Here, compounds of the formula IV—optionally in the form of their salts (HA)—are cyclized, preferably in the presence of a base, with a cyanide source V to give the desired imidazopyridines. Suitable acids HA are preferably HBr, HCl, trifluoroacetic acid (TFA) and sulfuric acid. Z is a good leaving group, preferably tosylate or bromide.

Compounds of the type of formula IV are commercially available or can be obtained according to scheme 3a.

Scheme 3a:

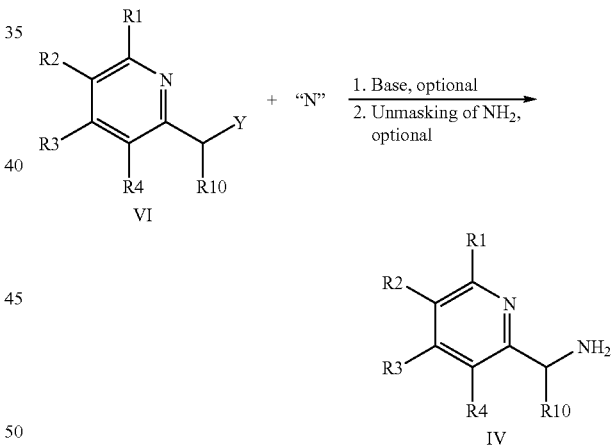

The starting materials II and III, where III is optionally present in the form of a salt, are reacted here at RT or a slightly elevated temperature of 40° C. to 60° C., advantageously in the presence of a base, preferably Hünig's base, in a solvent, preferably dimethylformamide (DMF), to give the compound of the formula I. The radicals R1 to R10 are as defined in formula I, Y corresponds to a good leaving group such as chloride, bromide, mesylate or tosylate, preferably bromide or mesylate.

Compounds of the formula II are commercially available or can be obtained according to processes known from the literature. Access to pentafluorosulfanyl derivatives of the formula II is described below.

Compounds of the formula III can be prepared according to scheme 2 (see also DE 2211796).

Here, pyridines of type VI are converted in the presence of a nitrogen nucleophile "N", and optionally of a subsequent reaction for the unmasking of the —$NH_2$ group, to the pyridylmethylamines IV. Suitable nitrogen nucleophiles here are ammonia, which leads directly, without further unmasking, to the compounds of type IV, azides, such as sodium azide, which has to be subsequently reduced for the establishment of the amino function, for which triphenylphosphine (Bioorg. Med. Chem. Lett. 2925, 2002) or noble metal catalysts such as palladium or platinum in the presence of hydrogen are suitable (J. Med. Chem. 5005, 2002), phthalimide, which subsequently has to be treated with hydrazine for the unmasking of the amino function (J. Med. Chem. 1315, 2004), or urotropin, which has to be treated with acid, preferably hydrochloric acid, for the unmasking of the amino function (Synthesis 2145, 2003). The radicals R1 to R4, R10 and Y are as defined above, where Y here can also be —OH, which is activated in situ to a good leaving group, which is then subsequently substituted by one of the abovementioned nitrogen nucleophiles (Chem. Pharm. Bull. 1493, 1989; Bioorg. Med. Chem. Lett. 2463, 2004).

Further access to amines of type IV is shown in scheme 3b.

Scheme 3b:

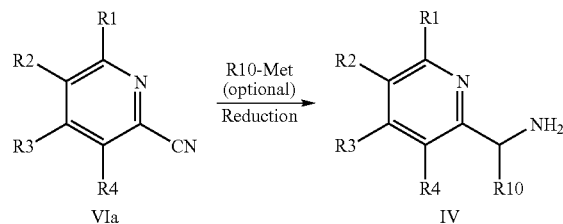

Starting from 2-cyanopyridines of type VIa, the nitrile function is reduced using reductants such as hydrogen in the presence of metal catalysts such as palladium or Raney nickel to give the amines of type IV. If the nitrile function is reacted before reduction with organometallic reagents such as Grignard or organolithium compounds, the substituent R10 can be introduced in this way. The imines intermediately obtained thereby can be reduced to the amines IV by sodium borohydride, sodium triacetoxyborohydride or sodium cyanoborohydride. The radicals R1 to R4 and R10 are as defined above. Met is —Li or —MgBr.

Alternatively, compounds of the formula (I) as shown in scheme 4 can be prepared.

Scheme 4:

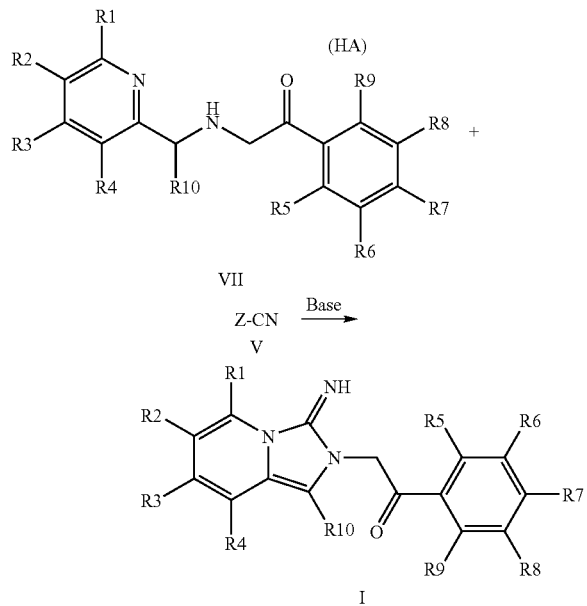

Here, compounds of the formula VII—optionally in the form of their salts (HA)—are cyclized in a solvent such as water, methanol, ethanol, acetic acid, acetonitrile, toluene or suitable mixtures of these solvents, preferably toluene, in the presence of a base, preferably Hünig's base, using a cyanide source V, preferably cyanogen bromide, to give the desired imidazopyridines.

Compounds of the formula VII are obtained according to scheme 5, by reacting amines of the formula III with acetophenone derivatives of the type of formula II. This is preferably carried out in solvents such as DMF, tetrahydrofuran (THF) or acetonitrile, preferably in THF. Suitable bases are Hünig's base, lithium hexamethyldisilazane or potassium carbonate, preferably lithium hexamethyldisilazane. The radicals here are as defined above.

Scheme 5:

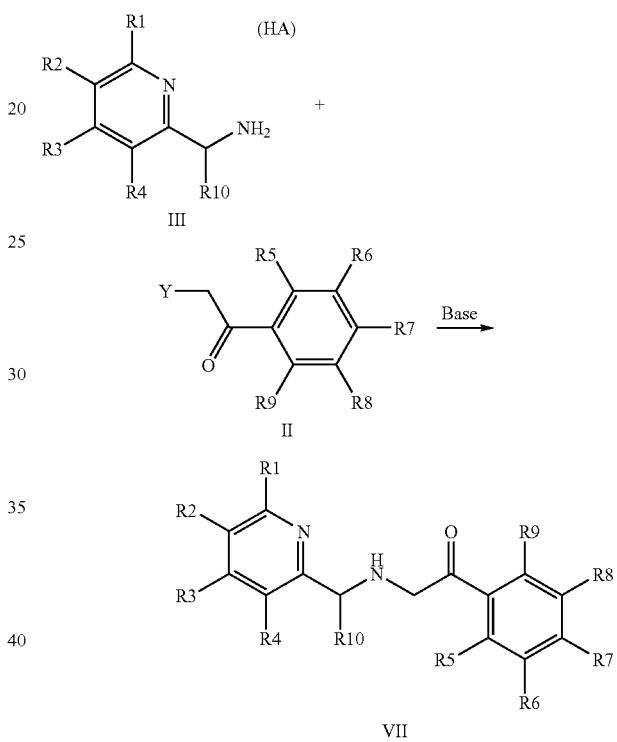

Alternatively, compounds of the formula VII can be obtained according to scheme 6, by reacting amines of the formula IX with pyridyl derivatives of the type of formula VIII. The reaction is carried out in solvents such as DMF, THF, acetonitrile or ethanol, preferably THF. Suitable bases are Hünig's base, lithium hexamethyldisilazane or potassium carbonate, preferably lithium hexamethyldisilazane. The radicals here are as defined above.

Scheme 6:

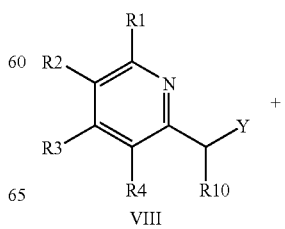

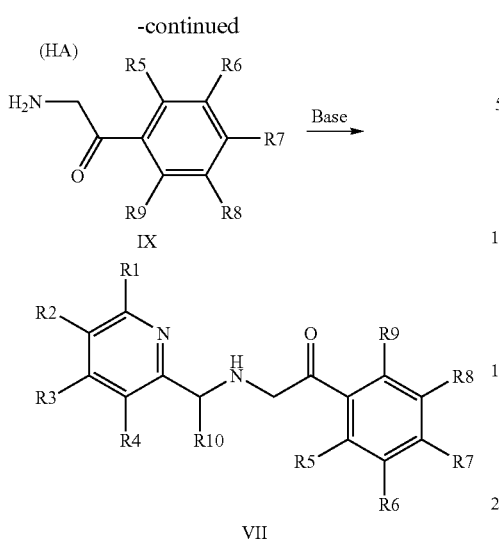

If one of the radicals R5, R6, R7, R8 or R9 is a pentafluorosulfanyl (—SF₅), these compounds of the type of formula IIa (Y=Br) can be prepared as described in scheme 7.

Scheme 7:

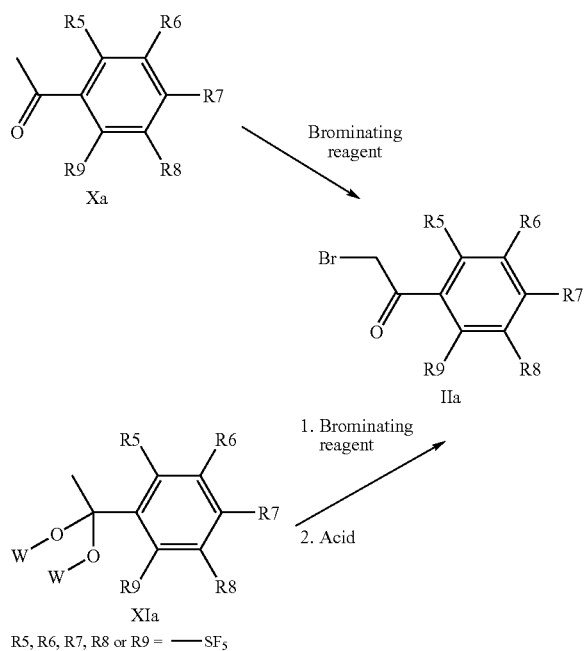

Here, the acetophenone derivatives of the formula Xa can either be brominated directly, for example with Br₂, N-bromosuccinimide (NBS) or phenyltrimethyl tribromide, preferably in glacial acetic acid, methanol or methanol/THF mixtures, to give compounds of the formula IIa or else the corresponding ketals of the compound of the formula XIa of the acetophenone derivatives X are brominated using, for example, the above brominating reagents, preferably phenyltrimethyl tribromide. Subsequently, in order to obtain the compounds of the formula IIa, the ketals are cleaved in the presence of acid, for example hydrochloric acid, hydrobromic acid, sulfuric acid, trifluoroacetic acid, preferably sulfuric acid.

The ketals of the formula XI, XIa and XI' can be obtained starting from the ketones of the formula X by ketalization reactions known to the person skilled in the art. Preferably, the reaction to give the compounds of the formula XI is carried out in methanol with methyl orthoformate in the presence of DL-10-camphorsulfonic acid (scheme 8).

Scheme 8:

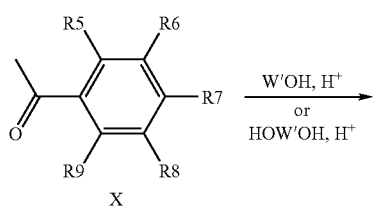

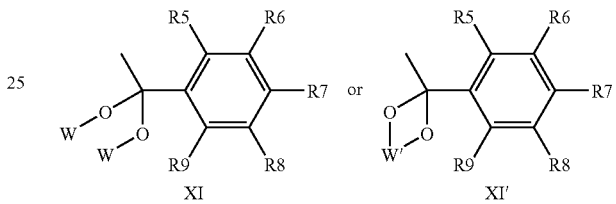

The radicals R5 to R9 here are as defined above. The radical W corresponds to a —($C_1$-$C_4$)-alkyl group. The radical W' corresponds to ethylene, propylene or butylene or, together with the group —O—C—O—, forms a 1,3-dioxo ring of ring size 5, 6 or 7. Ketals of this type are obtained by reaction with alkylene glycols such as ethylene glycol in the presence of acids such as sulfuric acid or para-toluenesulfonic acid and/or dehydrating agents. In the simplest case, the reaction is carried out in toluene in the presence of catalytic amounts of para-toluenesulfonic acid in a water separator.

More complex substituted compounds of the formula Xa with R5, R6, R7, R8 or R9 equal to pentafluorosulfanyl and with a further R5, R6, R7, R8 or R9 unequal to hydrogen can be obtained starting from commercially available pentafluorosulfanyl derivatives. Derivatives not commercially available can be obtained in analogy to known preparation processes (Tetrahedron 56 (2000) 3399; Organic Letters 4 (17) (2002) 3013; WO 2005/047240). For the previously undescribed 1-(3-dimethylamino-5-pentafluorosulfanylphenyl)ethanone, a synthesis route is shown in scheme 9.

Scheme 9:

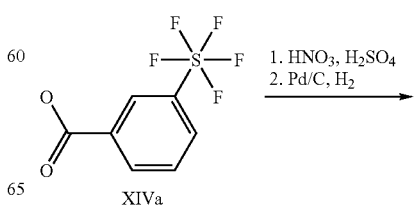

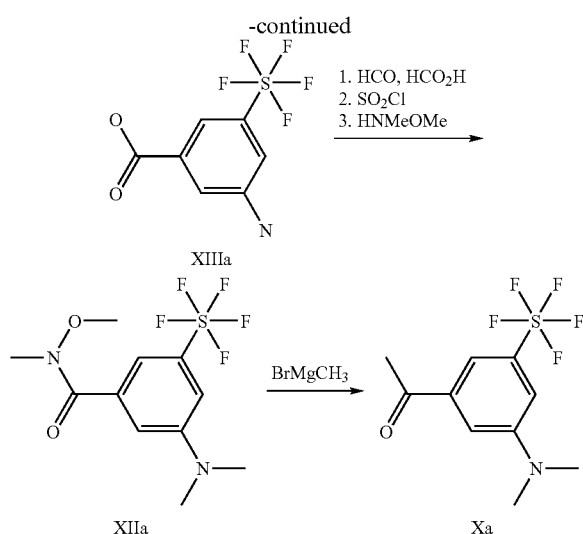

Using reactions known to the person skilled in the art, starting from commercially available 3-(pentafluorosulfanyl) benzoic acid XIVa, this was first nitrated and subsequently reduced to the amine using palladium on carbon in the presence of hydrogen. The 3-amino-5-pentafluorosulfanylbenzoic acid XIIIa obtained was then dimethylated on the amine nitrogen under Eschweiler-Clark conditions, and the carboxylic acid was converted to the acid chloride using thionyl chloride and subsequently reacted with O,N-dimethylhydroxylamine. The 3-dimethylamino-N-methoxy-N-methyl-5-pentafluorosulfanylbenzamide XIIa thus obtained was converted to the corresponding pentafluorosulfanyl derivatives of the formula Xa using methylmagnesium bromide.

A compound of the formula I prepared according to schemes 1 or 4, or a suitable precursor of the formula I which on account of its chemical structure occurs in enantiomeric forms, can be separated into the pure enantiomers by salt formation using enantiomerically pure acids or bases, chromatography on chiral stationary phases or derivatization by means of chiral enantiomerically pure compounds such as amino acids, separation of the diastereomers thus obtained and removal of the chiral auxiliary groups (process c), or the compound of the formula I prepared according to schemes 1 or 4 can either be isolated in free form or, in the case of the presence of acidic or basic groups, converted into physiologically tolerable salts (process d).

Acidic or basic products of the compound of the formula I can be present in the form of their salts or in free form. Pharmacologically tolerable salts are preferred, for example alkali metal or alkaline earth metal salts or hydrochlorides, sulfates, hemisulfates, methylsulfonates, p-toluenesulfonates, all possible phosphates, and salts of the amino acids, natural bases or carboxylic acids such as lactates, citrates, tartrates, acetates, adipates, fumarates, gluconates, glutamates, maleates or pamoates.

The preparation of physiologically tolerable salts from compounds of the formula I capable of salt formation, including their stereoisomeric forms, according to process step c) is carried out in a manner known per se. If compounds of the formula I contain acidic functionality, stable alkali metal, alkaline earth metal or optionally substituted ammonium salts can be formed with basic reagents such as hydroxides, carbonates, hydrogencarbonates, alcoholates and ammonia or organic bases, for example trimethyl- or triethylamine, ethanolamine, diethanolamine or triethanolamine, trometamol or even basic amino acids, for example lysine, ornithine or arginine. Basic groups of the compounds of the formula I form acid addition salts with acids. Both inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

In process step d), the compound of the formula I, if it occurs as a mixture of diastereomers or enantiomers or is formed as their mixtures in the chosen synthesis, is separated into the pure stereoisomers, either by chromatography on an optionally chiral carrier material, or, if the racemic compound of the formula I is capable of salt formation, a fractional crystallization of the diastereomeric salts formed can also be carried out using an optically active base or acid as an auxiliary. Suitable chiral stationary phases for the thin-layer or column chromatographic separation of enantiomers are, for example, modified silica gel carriers ("Pirkle phases") and high molecular weight carbohydrates such as triacetylcellulose. For analytical purposes, appropriate derivatizations known to the person skilled in the art, also gas chromatographic methods on chiral stationary phases, can be used. For the separation of enantiomers of the racemic carboxylic acids, the differently soluble diastereomeric salts are formed using an optically active, usually commercially obtainable base such as (−)-nicotine, (+)- and (−)-phenylethylamine, quinine bases, L-lysine or L- and D-arginine, the more poorly soluble component is isolated as a solid, the more easily soluble diastereomer is precipitated from the mother liquor and the pure enantiomers are obtained from the diastereomeric salts thus obtained. In principally the same way, the racemic compounds of the formula I which contain a basic group, such as an amino group, can be converted to the pure enantiomers using optically active acids, such as (+)-camphor-10-sulfonic acid, D- and L-tartaric acid, D- and L-lactic acid and (+) and (−)-mandelic acid. Chiral compounds which contain alcohol or amine functions can also be converted to the corresponding esters or amides using appropriately activated or optionally N-protected enantiomerically pure amino acids, or conversely chiral carboxylic acids can be converted to the amides using carboxy-protected enantiomerically pure amino acids or converted to the corresponding chiral esters using enantiomerically pure hydroxycarboxylic acids such as lactic acid. The chirality of the amino acid or alcohol radical introduced in enantiomerically pure form can then be utilized for the separation of the isomers by carrying out a separation of the diastereomers now present by crystallization or chromatography on suitable stationary phases and then removing again the chiral moiety brought along by means of suitable methods.

Furthermore, the possibility results in the case of some of the compounds according to the invention of employing diastereomerically or enantiomerically pure starting products for the preparation of the skeleton structures. Other or simplified processes can thus also be employed for the purification of the end products. These starting products were prepared in enantiomerically or diastereomerically pure form beforehand according to processes known from the literature. This can in particular mean that in the synthesis of the skeleton structures either enantioselective processes are used, or else an enantiomer (or diastereomer) separation is carried out at an earlier synthesis stage and not only in the stage of the end products.

Likewise, a simplification of the separations can be achieved by proceeding in two or more stages.

The invention also relates to medicaments which comprise an efficacious amount of at least one compound of the formula I and/or of a physiologically tolerable salt of the compound of the formula I and/or an optionally stereoisomeric form of the compound of the formula I, together with a pharmaceutically suitable and physiologically tolerable vehicle, additive and/or other active ingredients and excipients.

On account of the pharmacological properties, the compounds according to the invention are suitable, for example, for the prophylaxis, secondary prevention and therapy of all diseases of the type which are treatable by inhibition of the protease-activated receptor 1 (PAR1). Thus the compounds according to the invention are suitable both for prophylactic and therapeutic use in humans. They are suitable both for acute treatment and long-term therapy. The compounds of the formula I can be employed in patients who are suffering from disturbances of well-being or illnesses which are accompanied by thromboses, embolisms, hypercoagulability or fibrotic changes.

These include myocardial infarct, angina pectoris and all other forms of acute coronary syndrome, stroke, peripheral vascular disorders, deep vein thrombosis, pulmonary embolism, embolic or thrombotic events caused by cardiac arrhythmias, cardiovascular events such as restenosis after revascularization, angioplasty and similar interventions such as stent implantations and bypass operations. Furthermore, the compounds of the formula I can be employed in all interventions which lead to contact of the blood with foreign surfaces such as in dialysis patients and patients having indwelling catheters. Compounds of the formula I can be employed in order to reduce the risk of thrombosis after surgical interventions such as in knee and hip joint operations.

Compounds of the formula I are suitable for the treatment of patients with disseminated intravascular coagulation, sepsis and other intravascular events which accompany inflammation. Furthermore, compounds of the formula I are suitable for the prophylaxis and treatment of patients with atherosclerosis, diabetes and the metabolic syndrome and their sequelae. Disorders of the hemostatic system (for example fibrin deposits) were implicated in mechanisms which lead to tumor growth and tumor metastasis, and in inflammatory and degenerative joint disorders such as rheumatoid arthritis and arthrosis. Compounds of the formula I are suitable for the retardation or prevention of processes of this type.

Further indications for the use of the compounds of the formula I are fibrotic changes of the lung, such as chronic obstructive pulmonary disease, adult respiratory distress syndrome (ARDS) and of the eye such as fibrin deposits after eye operations. Compounds of the formula I are also suitable for the prevention and/or treatment of scar formation.

The medicaments according to the invention can be administered by oral, inhalative, rectal or transdermal administration or by subcutaneous, intraarticular, intraperitoneal or intravenous injection. Oral administration is preferred. Coating of stents with compounds of the formula I and other surfaces which come into contact with blood in the body is possible.

The invention also relates to a process for the production of a medicament, which comprises bringing at least one compound of the formula I into a suitable administration form with a pharmaceutically suitable and physiologically tolerable vehicle and optionally further suitable active ingredients, additives or excipients. Suitable solid or galenical preparation forms are, for example, granules, powders, coated tablets, tablets, (micro)capsules, suppositories, syrups, juices, suspensions, emulsions, drops or injectable solutions and preparations having protracted release of active ingredient, in whose preparation customary excipients such as vehicles, disintegrants, binders, coating agents, swelling agents, glidants or lubricants, flavorings, sweeteners, and solubilizers are used. Frequently used excipients which may be mentioned are magnesium carbonate, titanium dioxide, lactose, mannitol and other sugars, talc, milk protein, gelatin, starch, cellulose and its derivatives, animal and vegetable oils such as fish liver oil, sunflower oil, peanut oil or sesame oil, polyethylene glycol and solvents such as, for example, sterile water and mono- or polyhydric alcohols such as glycerol.

Preferably, the pharmaceutical preparations are produced and administered in dose units, where each unit contains as an active constituent a certain dose of the compound of the formula I according to the invention. In the case of solid dose units such as tablets, capsules, coated tablets or suppositories, this dose can be up to about 1000 mg, but preferably approximately 50 to 300 mg, and in the case of injection solutions in ampoule form up to approximately 300 mg, but preferably approximately 10 to 100 mg.

For the treatment of an adult patient weighing approximately 70 kg, depending on the efficacy of the compound according to formula I, daily doses of approximately 2 mg to 1000 mg of active ingredient, preferably approximately 50 mg to 500 mg, are indicated. Under certain circumstances, however, higher or lower daily doses may also be applied. The administration of the daily dose can take place both by single administration in the form of an individual dose unit or else a number of smaller dose units and by multiple administration of subdivided doses at certain intervals.

Compounds of the formula I can be administered both as a monotherapy and in combination or together with all anti-thrombotics (anticoagulants and platelet aggregation inhibitors), thrombolytics (plasminogen activators of any type), other pro-fibrinolytically active substances, blood pressure-lowering agents, blood sugar regulators, lipid-lowering agents and antiarrhythmics.

EXAMPLES

End products were usually characterized by a chromatographic-mass spectroscopic method (LCUV/ESI-MS coupling) and $^1$H-NMR. The compounds are described by indication of the associated retention time in the ion stream (LCMS-rt) and of the corresponding M+H$^+$ signal in the associated mass spectrum. If it was not possible to obtain any M+H$^+$ mass signal under the conditions described, the $^1$H-NMR data were indicated alternatively. Abbreviations used are either explained or correspond to the customary conventions. If not stated otherwise, chromatographic separations were carried out on silica gel using ethyl acetate/heptane or DCM/methanol mixtures as an eluent.

The evaporation of solvents usually took place under reduced pressure at 35° C. to 45° C. on a rotary evaporator and is described by "freed from the solvent", "concentrated" or "solvent removed".

If not mentioned otherwise, the LCUV/MS analyses were carried out under the following conditions:

Column: YMC J'shere ODS H80 20 × 2.1 mm, Waters GmbH, Helfmann-Park 10, 65760 Eschborn, Germany; packing material 4 µm, -continued

| | |
|---|---|
| Eluent: | ACN:H₂O + 0.05% TFA (flow 1 ml/min) |
| Gradient: | 4:96 (0 min) → 95:5 (2 min) → 95:5 (2.4 min) → 4:96 (2.45 min) |
| Ionization: | ESI⁺ |

Deviating from this, LCUV/MS analyses—marked in the text by "method B"—were carried out under the following conditions:

| | |
|---|---|
| Column: | YMC J'sphere 33 × 2; packing material 4 μM |
| Eluent: | ACN + 0.05% TFA: H₂O + 0.05% TFA (flow 1 ml/min) |
| Gradient: | 5:95(0 min) → 95:5(2.5 min) → 95:5(3.0 min) |
| Ionization: | ESI⁺ |

Preparative HPLC using reversed-phase (RP) silica gel was carried out using the following methods:

Method A, standard method if none other is mentioned in the text

| Method A, standard method if none other is mentioned in the text | |
|---|---|
| Column: | Merck (Darmstadt, Germany) Purosphere ® RP18 25 × 250 mm, 10 μm |
| Solvent: | ACN:H₂O + 0.05% TFA (flow 25 ml/min) |
| Gradient: | 10:90 (0 min) → 90:10 (40 min) |
| Method B | |
| Column: | Merck Purosphere ® RP18 25 × 250 mm, 10 μm |
| Solvent: | ACN:H₂O + 0.05% TFA (flow 25 ml/min) |
| Gradient: | 0:100 (0 min) → 0:100 (5 min) → 20:80 (20 min) |

The reactions took place in standard reaction apparatuses such as single- or multi-necked flasks which, if not described otherwise, appropriate to the need, held 5 ml to 2000 ml and, depending on requirement, were equipped with a septum, stopper, condenser, stirrer or other articles of equipment. If not mentioned otherwise, all reactions took place under argon as a protective gas and were stirred using magnetic stirrers.

| Abbreviations used: | |
|---|---|
| abs. | absolute |
| ACN | acetonitrile |
| Boc | butoxycarbonyl |
| DCM | dichloromethane |
| DIPEA | N,N-diisopropylethylamine (Hünig's base) |
| DMF | dimethylformamide |
| DMSO | dimethyl sulfoxide |
| LCMS-Rt | retention time of the compound in the ion stream |
| LCUV/MS | liquid chromatography-ultraviolet/mass spectroscopy |
| MeOH | methanol |
| RT | room temperature (20° C. to 25° C.) |
| TFA | trifluoroacetic acid |
| THF | tetrahydrofuran |

Example 1

1-(3,5-Di-tert-butyl-4-hydroxyphenyl)-2-(3-imi-noimidazo[1,5-a]pyridin-2-yl)ethanone as the trifluoroacetic acid salt

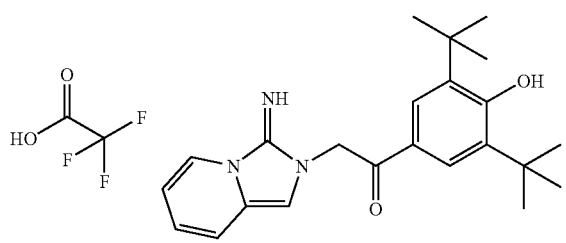

1a) 1-(3,5-Di-tert-butyl-4-hydroxyphenyl)-2-[(pyridin-2-ylmethyl)amino]ethanone hydrobromide

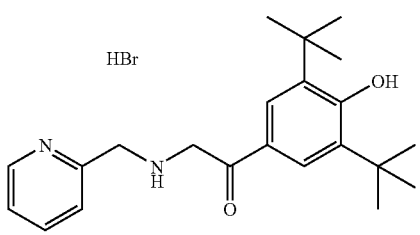

2-(Aminomethyl)pyridine (100 mg) was initially introduced in absolute THF (12 ml) and treated with lithium hexamethyldisilazane solution (1.01 ml, 1 M in THF) at RT with stirring and under argon. After 30 min, 2-bromo-1-(3,5-di-tert-butyl-4-hydroxyphenyl)ethanone (0.5 eq., 151 mg, dissolved in 1.5 ml absolute THF) was added dropwise. For completion of the reaction, the remaining amount of bromide (151 mg) was added and after 2 hours the precipitate formed was filtered off with suction and dried. The 98 mg of the title compound obtained are contaminated with small amounts of THF which, however, do not interfere with the further reaction.

LCMS-Rt: 1.21 min [M+H⁺]: 355.1

1b) 1-(3,5-Di-tert-butyl-4-hydroxyphenyl)-2-(3-imi-noimidazo[1,5-a]pyridin-2-yl)ethanone as the trifluoroacetic acid salt 1-(3,5-Di-tert-butyl-4-hydroxyphenyl)-2-[(pyridin-2-ylmethyl)amino]ethanone hydrobromide (95 mg) was dissolved in water. After addition of saturated sodium hydrogencarbonate solution, the mixture was extracted with ethyl acetate (three times). The combined ethyl acetate phases were dried over magnesium sulfate, filtered and concentrated. 67 mg of the free base were obtained.

This was taken up with toluene (5 ml) and treated with stirring with cyanogen bromide (22 mg, dissolved in 1.5 ml of toluene). After 1.5 h the solvent was concentrated and the residue was purified by means of preparative HPLC. The product-containing fractions were combined, freed of acetonitrile and freeze-dried. 40 mg of the desired compound were obtained.

LCMS-Rt: 1.30 min [M+H⁺]: 380.1

Alternatively, 1-(3,5-di-tert-butyl-4-hydroxyphenyl)-2-(3-iminoimidazo[1,5-a]pyridin-2-yl)ethanone can be prepared as the trifluoroacetic acid salt as follows:

1c) Imidazo[1,5-a]pyridin-3-ylamine as the trifluoroacetic acid salt

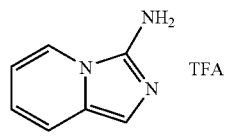

2-Aminomethylpyridine (1 g) was dissolved in abs. toluene (5 ml) and treated with stirring with cyanogen bromide (1 g), dissolved in abs. toluene (5 ml). After stirring at RT for 4 h, the mixture was allowed to stand over the weekend. The solvent was then decanted from the resulting precipitate and the residue was washed with acetonitrile. Approximately 300 mg of 1.7 g of the precipitate were subsequently purified by means of preparative HPLC (method B). The product-containing fractions were combined, freed from acetonitrile and freeze-dried. 74 mg of the desired compound were obtained.

LCMS-Rt: 0.34 min [M+H$^+$]: 134.1

1d) 1-(3,5-Di-tert-butyl-4-hydroxyphenyl)-2-(3-iminoimidazo[1,5-a]pyridin-2-yl)ethanone as the trifluoroacetic acid salt Imidazo[1,5-a]pyridin-3-ylaminetrifluoroacetic acid salt (10 mg) was dissolved at RT and with stirring in abs. DMF (1.5 ml) and treated with Hünig's base (7 µl). 2-Bromo-1-(3,5-di-tert-butyl-4-hydroxyphenyl)ethanone (14 mg, dissolved in 0.5 ml of DMF) was then added dropwise. After stirring at RT for 4 h, the mixture was allowed to stand overnight and was then treated with saturated common salt solution and extracted three times with ethyl acetate. The combined organic phases were dried over magnesium sulfate, filtered and concentrated. Residues of DMF were eliminated in a high vacuum. The crude product obtained was purified by means of preparative HPLC. The product-containing fractions were combined, freed from the acetonitrile and freeze-dried. 9 mg of the desired compound were obtained. LCMS-Rt: 1.33 min [M+H$^+$]: 380.2

Example 2

2-(3-Iminoimidazo[1,5-a]pyridin-2-yl)-1-(3-pentafluorosulfanylphenyl)ethanone as the trifluoroacetic acid salt

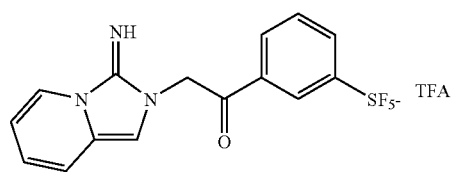

2a) 2-Bromo-1-(3-pentafluorosulfanylphenyl)ethanone

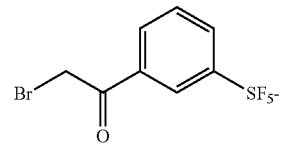

3-Pentafluorosulfanylacetophenone (400 mg) was initially introduced in glacial acetic acid (10 ml) and bromine (91 µl, dissolved in 1 ml of glacial acetic acid) was slowly added dropwise. After stirring at RT for 4 hours, the mixture was allowed to stand overnight and then freed from the solvent. The residue was taken up twice with toluene and brought to dryness. The crude product obtained was purified by means of preparative HPLC. The product-containing fractions were combined, freed from the acetonitrile and freeze-dried. 252 mg of the desired compound were obtained.

LCMS-Rt: 1.69 min [M+H$^+$]: 324.9

2b) 2-(3-Iminoimidazo[1,5-a]pyridin-2-yl)-1-(3-pentafluorosulfanylphenyl)-ethanone as the trifluoroacetic acid salt Imidazo[1,5-a]pyridin-3-ylamine as the trifluoroacetic acid salt (20 mg, Example 1c) was reacted according to Example 1d) with 2-bromo-1-(3-pentafluorosulfanylphenyl)ethanone (26 mg) in the presence of Hünig's base. Instead of DMF, THF was used as the solvent. 25 mg of the desired compound were isolated.

LCMS-Rt: 1.13 min [M+H$^+$]: 378.0

Example 3

2-(1-Cyclopropyl-3-iminoimidazo[1,5-a]pyridin-2-yl)-1-(3,5-di-tert-butyl-4-hydroxyphenyl)ethanone as the trifluoroacetic acid salt

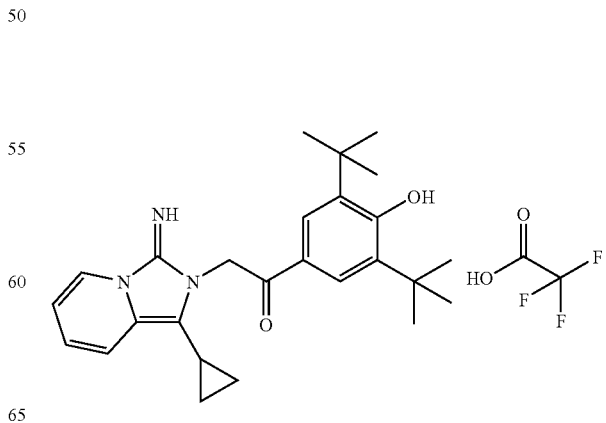

3a) 2-[(Cyclopropylpyridin-2-ylmethyl)amino]-1-(3,5-di-tert-butyl-4-hydroxyphenyl)ethanone

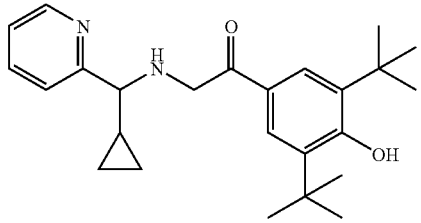

C-Cyclopropyl-C-pyridin-2-ylmethylamine (200 mg) was almost completely dissolved in abs. THF (15 ml) with stirring. After addition of lithium hexamethyldisilazane solution (1.8 ml, 1 M in THF), 30 min later 2-bromo-1-(3,5-di-tert-butyl-4-hydroxyphenyl)ethanone (296 mg, dissolved in 3 ml of abs. THF) was added dropwise. After stirring for 2 h, water was added and the aqueous phase was extracted three times with ethyl acetate. The combined ethyl acetate phases were dried over magnesium sulfate, filtered and concentrated. The crude product obtained was purified by means of preparative HPLC. The product-containing fractions were combined, freed from the acetonitrile, rendered basic with saturated potassium carbonate solution and extracted three times with ethyl acetate. The combined ethyl acetate phases were dried over magnesium sulfate, filtered and concentrated.

13 mg of the desired compound were obtained.
LCMS-Rt: 1.33 min [M+H$^+$]: 395.1

3b) 2-(1-Cyclopropyl-3-iminoimidazo[1,5-a]pyridin-2-yl)-1-(3,5-di-tert-butyl-4-hydroxyphenyl)ethanone as the trifluoroacetic acid salt 2-[(Cyclopropylpyridin-2-ylmethyl)amino]-1-(3,5-di-tert-butyl-4-hydroxyphenyl)ethanone (13 mg) were cyclized with cyanogen bromide (4 mg) in toluene as described in Example 1b). 4 mg of the desired compound were obtained.
LCMS-Rt: 1.42 min [M+H$^+$]: 420.2

Example 4

1-(3,5-Di-tert-butyl-4-hydroxyphenyl)-2-(3-imino-1-phenylimidazo[1,5-a]pyridin-2-yl)ethanone as the trifluoroacetic acid salt

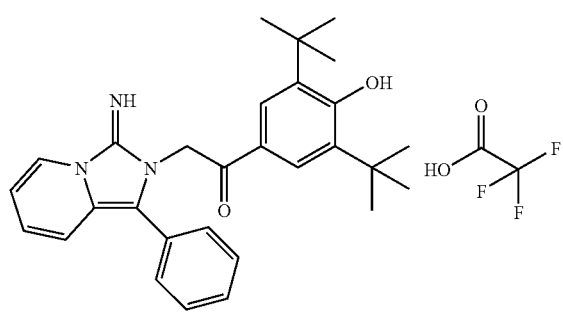

4a) 1-(3,5-Di-tert-butyl-4-hydroxyphenyl)-2-[(phenylpyridin-2-ylmethyl)amino]-ethanone as the trifluoroacetic acid salt

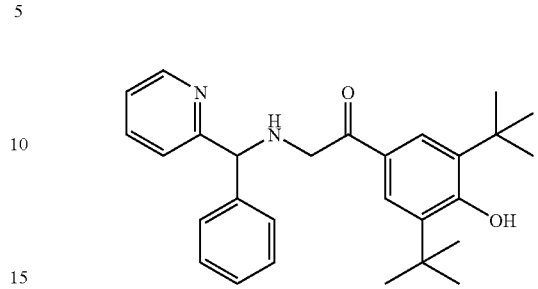

Phenyl(2-pyridyl)methylamine hydrochloride (150 mg) was dissolved in a little water, rendered alkaline with saturated sodium hydrogencarbonate solution and extracted three times with ethyl acetate. The combined ethyl acetate phases were dried over magnesium sulfate, filtered and concentrated. 113 mg of the free base were obtained. Of this, 55 mg were dissolved in THF (4 ml) and 2-bromo-1-(3,5-di-tert-butyl-4-hydroxyphenyl)ethanone (96 mg, dissolved in 2 ml THF) was added dropwise with stirring. After stirring at RT for 4 h, the mixture was allowed to stand overnight and then the precipitate formed was filtered off. The mother liquor was concentrated and purified by means of preparative chromatography. The product-containing fractions were combined, freed from the acetonitrile and freeze-dried. 12 mg of the desired compound were isolated.

LCMS-Rt: 1.40 min [M+H$^+$]: 431.3

4b) 1-(3,5-Di-tert-butyl-4-hydroxyphenyl)-2-(3-imino-1-phenylimidazo[1,5-a]pyridin-2-yl)ethanone as the trifluoroacetic acid salt 1-(3,5-Di-tert-butyl-4-hydroxyphenyl)-2-[(phenylpyridin-2-ylmethyl)amino]ethanone-trifluoroacetic acid salt (12 mg) was reacted in toluene analogously to Example 1b). 3 mg of the desired compound were obtained.
LCMS-Rt: 1.50 min [M+H$^+$]: 456.2

Example 5

1-(3,5-Di-tert-butyl-4-hydroxyphenyl)-2-(3-imino-8-methyl imidazo[1,5-a]pyridin-2-yl)ethanone as the trifluoroacetic acid salt or hydrobromide

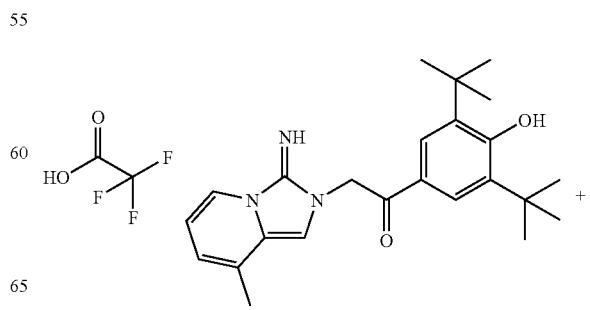

-continued

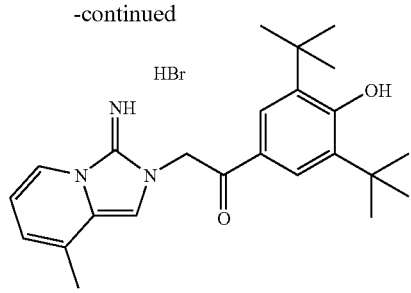

5a) 8-Methylimidazo[1,5-a]pyridin-3-ylamine as the trifluoroacetic acid salt

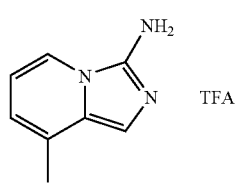

2-Aminomethyl-3-methylpyridine (500 mg) was dissolved in abs. toluene (15 ml) and cyanogen bromide (455 mg, dissolved in 5 ml toluene) was added dropwise with stirring. After one hour, the precipitate was filtered off with suction and the mother liquor was discarded. The precipitate and the sticky flask residue were purified by means of preparative HPLC. The product-containing fractions were combined, freed from the acetonitrile and freeze-dried. 191 mg of the desired compound were isolated as the trifluoroacetic acid salt.

LCMS-Rt: 0.68 min [M+H$^+$]: 148.1

5b) 1-(3,5-Di-tert-butyl-4-hydroxyphenyl)-2-(3-imino-8-methylimidazo[1,5-a]pyridin-2-yl)ethanone as the hydrobromide or 1-(3,5-di-tert-butyl-4-hydroxyphenyl)-2-(3-imino-8-methylimidazo[1,5-a]pyridin-2-yl)ethanone as the trifluoroacetic acid salt 8-Methylimidazo[1,5-a]pyridin-3-ylamine (30 mg as the trifluoroacetic acid salt) was dissolved in abs. THF (5 ml), treated with Hünig's base (19 µl) and 2-bromo-1-(3,5-di-tert-butyl-4-hydroxyphenyl)ethanone (38 mg, dissolved in 1.5 ml abs. THF) was slowly added dropwise. After stirring at RT for 2 hours, the mixture was allowed to stand overnight and then warmed to 60° C. to complete the reaction and a little bromide (4 mg) was again added. The precipitate formed was filtered off with suction and dried. 8.5 mg of the title compound were obtained as the hydrobromide.

LCMS-Rt: 1.30 min [M+H$^+$]: 394.2

For the obtainment of the trifluoroacetic acid salt, the mother liquor was concentrated and purified by means of preparative HPLC. The product-containing fractions were combined, freed from the acetonitrile and freeze-dried. 23 mg of the desired compound were obtained as the trifluoroacetic acid salt.

LCMS-Rt: 1.30 min [M+H$^+$]: 394.2

Example 6a and 6b 1-(3,5-Di-tert-butyl-4-hydroxyphenyl)-2-(3-imino-7-trifluoromethylimidazo[1,5-a]pyridin-2-yl)ethanone as the trifluoroacetic acid salt (6a) or hydrobromide (6b)

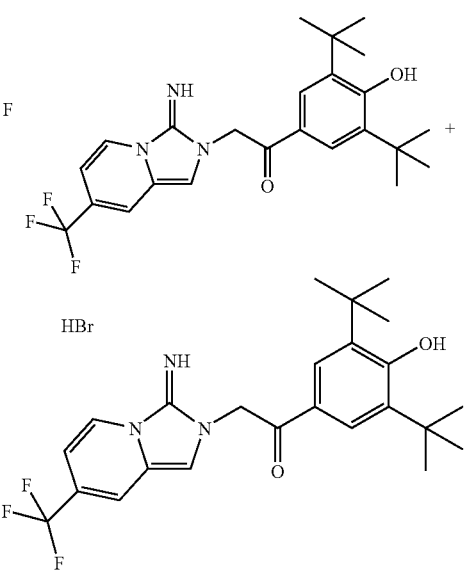

6a)

7-Trifluoromethylimidazo[1,5-a]pyridin-3-ylamine

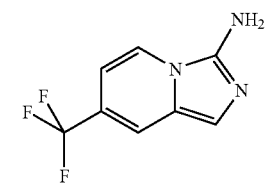

C-(4-Trifluoromethylpyridin-2yl)methylamine hydrochloride (600 mg) were dissolved in water, treated with saturated sodium hydrogencarbonate solution and then extracted three times with ethyl acetate. The combined ethyl acetate phases were dried over magnesium sulfate, filtered and concentrated. 300 mg of the free base were obtained. This was dissolved in abs. toluene (15 ml) and cyanogen bromide (191 mg, dissolved in 5 ml toluene) was slowly added dropwise. After 24 hours, the precipitate formed was filtered off with suction, dried and purified by means of preparative HPLC. The product-containing fractions were combined, freed from the acetonitrile and freeze-dried. 168 mg of the desired compound were obtained as the trifluoroacetic acid salt.

LCMS-Rt: 0.76 min [M+H$^+$]: 202.1

6b) 1-(3,5-Di-tert-butyl-4-hydroxyphenyl)-2-(3-imino-7-trifluoromethylimidazo[1,5-a]pyridin-2-yl)ethanone as the trifluoroacetic acid salt and hydrobromide 7-Trifluoromethylimidazo[1,5-a]pyridin-3-ylamine (25 mg) was reacted according to Example 5b). 11.6 mg of the hydrobromide and, after chromatography, 9 mg of the trifluoroacetic acid derivative were obtained.

TFA salt: LCMS-Rt: 1.38 min [M+H$^+$]: 448.2
HBr salt: LCMS-Rt: 1.38 min [M+H$^+$]: 448.2

Example 7

Methyl 2-[2-(3,5-di-tert-butyl-4-hydroxyphenyl)-2-oxoethyl]-3-imino-2,3-dihydroimidazo[1,5-a]pyridine-6-carboxylate as the trifluoroacetic acid salt

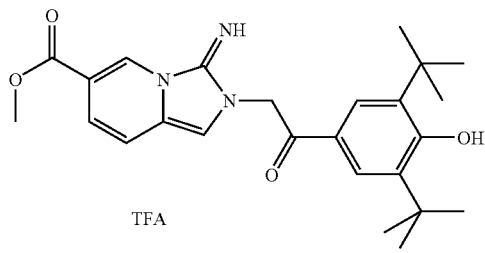

7a) 6-aminomethylnicotinic acid trifluoroacetate

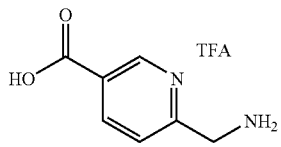

6-Cyanonicotinic acid as the trifluoroacetate (1 g) was dissolved in methanol (300 ml), treated with Raney nickel (0.224 g) and hydrogenated in a shaker autoclave at 80° C. for 20 h under 10 bar hydrogen pressure. Subsequently, the mixture was filtered, the residue was washed with a water/methanol mixture and the filtrate was concentrated. The residue was taken up with ACN/water and freeze-dried. 500 mg of product were obtained, which were sufficiently clean for use in the next stage.

LCMS-Rt: 0.14 min [M+H$^+$]: 153.1

7b) Methyl 6-aminomethylnicotinate as the trifluoroacetic acid salt

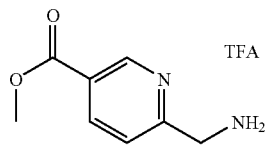

6-Aminomethylnicotinic acid trifluoroacetate (500 mg) was dissolved in methanol (45 ml). After addition of concentrated sulfuric acid (10 drops), the solution was refluxed for 24 h. After cooling, the solvent was stripped off and the residue was dissolved in water and purified by means of preparative HPLC. The product-containing fractions were combined, freed from the ACN and freeze-dried. 395 mg of the desired compound were obtained as the trifluoroacetic acid salt.

LCMS-Rt: 0.27 min [M+H$^+$]: 167.1

7c) Methyl 3-aminoimidazo[1,5-a]pyridine-6-carboxylate

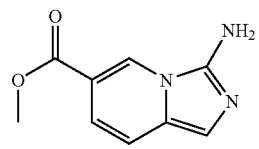

Methyl 6-aminomethylnicotinate trifluoroacetate (390 mg) was dissolved in toluene (35 ml) and treated with Hünig's base (230 µl). Cyanogen bromide (0.35 ml of a 5 M solution in acetonitrile) was then slowly added dropwise. After stirring at RT for 3 h, the solvent was stripped off and the residue was taken up with water and saturated sodium hydrogencarbonate solution and extracted three times with ethyl acetate. The combined organic phases were dried over sodium sulfate, filtered and concentrated. The residue was purified by means of preparative HPLC. The product-containing fractions were combined, freed from the acetonitrile and freeze-dried. The residue was then taken up with a little water, treated with saturated sodium hydrogencarbonate solution and extracted three times with ethyl acetate. The combined organic phases were dried over sodium sulfate, filtered and concentrated. 110 mg of the desired compound were obtained.

LCMS-Rt: 0.67 min [M+H$^+$]: 192.1

7d) Methyl 2-[2-(3,5-di-tert-butyl-4-hydroxyphenyl)-2-oxoethyl]-3-imino-2,3-dihydroimidazo[1,5-a]pyridine-6-carboxylate as the trifluoroacetic acid salt Methyl 3-aminoimidazo[1,5-a]pyridine-6-carboxylate (26 mg) was dissolved in abs. DMF (2.5 ml) and 2-bromo-1-(3,5-di-tert-butyl-4-hydroxyphenyl)ethanone (45 mg, dissolved in 1.5 ml of abs. DMF) was slowly added dropwise. After stirring for 5 hours, the reaction mixture was allowed to stand overnight and then further bromide (10 mg, dissolved in 0.5 ml of abs. DMF) was added to complete the reaction. After stirring for a further 2 h, the solvent was stripped off and the residue was purified by means of preparative HPLC. The product-containing fractions were combined, freed from the acetonitrile and freeze-dried. 50 mg of the desired compound were obtained as the trifluoroacetic acid salt.

LCMS-Rt: 1.30 min [M+H$^+$]: 438.3

Example 8

Methyl 2-[2-(3-tert-butyl-4-methoxy-5-morpholin-4-ylphenyl)-2-oxoethyl]-3-imino-2,3-dihydroimidazo[1,5-a]pyridine-6-carboxylate as the trifluoroacetic acid salt

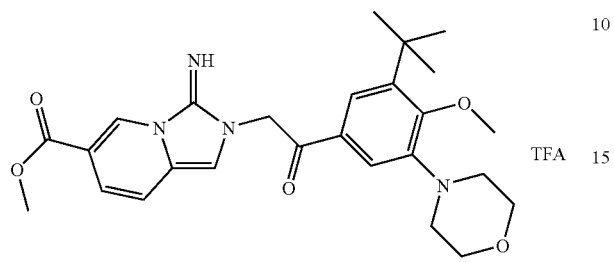

Methyl 3-aminoimidazo[1,5-a]pyridine-6-carboxylate (20 mg) was dissolved in abs. DMF (1 ml) and 2-bromo-1-(3-tert-butyl-4-methoxy-5-morpholin-4-ylphenyl)ethanone (45 mg, dissolved in 1 ml abs. DMF; prepared according to WO 2004/078721) was slowly added dropwise. After stirring at RT for 4 h, the mixture was additionally warmed to 40° C. for one hour. The reaction mixture was allowed to stand over the weekend and then the solvent was stripped off in a high vacuum. The residue was purified by means of preparative HPLC. The product-containing fractions were combined, freed from the acetonitrile and freeze-dried. 40 mg of the desired compound were obtained as the trifluoroacetic acid salt.

LCMS-Rt: 1.27 min [M+H$^+$]: 481.2

Example 9

1-(3-tert-Butyl-4-methoxy-5-morpholin-4-ylphenyl)-2-(3-iminoimidazo[1,5-a]pyridin-2-yl)ethanone as the trifluoroacetic acid salt

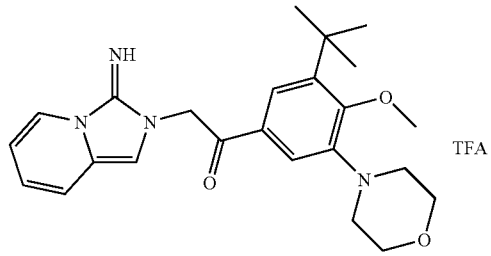

Imidazo[1,5-a]pyridin-3-ylamine as the trifluoroacetic acid salt (16 mg, Example 1c) was dissolved in abs. DMF (1 ml), treated with Hünig's base (31 µl), and 2-bromo-1-(3-tert-butyl-4-methoxy-5-morpholin-4-ylphenyl)ethanone (45 mg, dissolved in 1 ml of abs. DMF; prepared according to WO 2004/078721) was slowly added dropwise. After stirring at RT for 2 h, the mixture was allowed to stand overnight and then the solvent was stripped off in a high vacuum. The residue was purified by means of preparative HPLC. The product-containing fractions were combined, freed from the acetonitrile and freeze-dried. 12 mg of the desired compound were obtained as the trifluoroacetic acid salt.

LCMS-Rt: 1.28 min [M+H$^+$]: 423.3

Example 10

1-(3-tert-Butyl-4-methoxy-5-morpholin-4-ylphenyl)-2-(3-imino-8-methylimidazo[1,5-a]pyridin-2-yl)ethanone as the trifluoroacetic acid salt

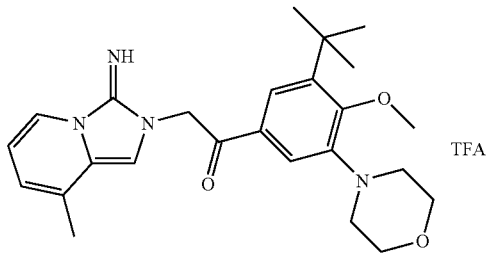

8-Methylimidazo[1,5-a]pyridin-3-ylamine as the trifluoroacetic acid salt (30 mg, Example 5a) was dissolved in abs. DMF (2 ml), treated with Hünig's base (19 µl) and 2-bromo-1-(3-tert-butyl-4-methoxy-5-morpholin-4-ylphenyl)ethanone (43 mg, dissolved in 1 ml of abs. DMF; prepared according to WO 2004/078721) was slowly added dropwise. After 4.5 h, further bromide (4 mg in 0.1 ml of DMF) was added to complete the reaction. After stirring for a further 3 h, the mixture was allowed to stand overnight and then the solvent was stripped off in a high vacuum. The residue was purified by means of preparative HPLC. The product-containing fractions were combined, freed from the acetonitrile and freeze-dried. 26 mg of the desired compound were obtained as the trifluoroacetic acid salt.

LCMS-Rt: 1.33 min [M+H$^+$]: 437.1

Example 11

1-(3-Dimethylamino-5-pentafluorosulfanylphenyl)-2-(3-iminoimidazo[1,5-a]pyridin-2-yl)ethanone as the trifluoroacetic acid salt

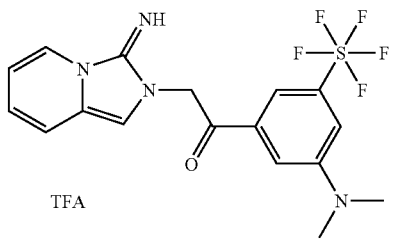

11a) 3-Amino-5-pentafluorosulfanylbenzoic acid

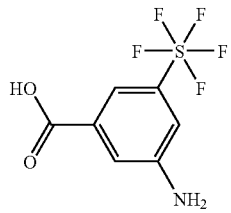

3-Pentafluorosulfanylbenzoic acid (3.0 g) was dissolved in fuming nitric acid (20 ml) and stirred at RT with exclusion of moisture. Concentrated sulfuric acid (1.5 ml) was then added and the mixture was stirred at 75° C. After stirring at 75° C. for 6 h, it was allowed to stand overnight, then further sulfuric acid (1.5 ml) was added and the mixture was heated at 75° C. for 8 h. After allowing to stand overnight, it was added to ice water and stirred for 2 h. The commencing crystallization was completed overnight in a refrigerator. The precipitate was then filtered off with suction and dried in a high vacuum. 2.7 g of 3-pentafluorosulfanyl-5-nitrobenzoic acid were obtained. It was possible to obtain a further 530 mg from the mother liquor after extracting three times with methylene chloride, drying the combined methylene chloride phases over magnesium sulfate and concentrating the solvent.

Subsequently, the 2.7 g were dissolved in methanol (70 ml), Raney nickel (approximately 500 mg) was added and the mixture was hydrogenated under a hydrogen atmosphere (hydrogen balloon). After 2 h, the catalyst was filtered off and the filter residue was washed well with methanol. The filtrate was concentrated and dried in a high vacuum. 2.3 g of crude product were obtained, which was reacted directly in the next stage.

LCMS-Rt: 1.21 min [M+H$^+$]: 264.0

11b) 3-Dimethylamino-5-pentafluorosulfanylbenzoic acid

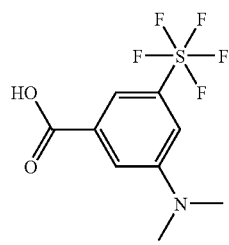

3-Amino-5-pentafluorosulfanylbenzoic acid (800 mg), formic acid (12 ml) and 37% strength formalin solution (8 ml) were in each case added to two microwave vessels. Both vessels were then heated at 110° C. for 30 min. After cooling, the solutions were combined and added to ice water. After extraction three times with ethyl acetate, the combined organic phases were dried with magnesium sulfate, filtered and concentrated. 1.76 g of the title compound were obtained, which were reacted directly in the next stage.

LCMS-Rt: 1.48 min [M+H$^+$]: 292.0

11c) 3-Dimethylamino-N-methoxy-N-methyl-5-pentafluorosulfanylbenzamide

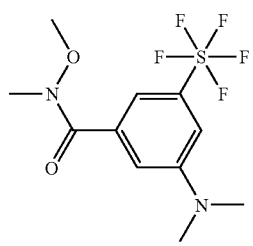

3-Dimethylamino-5-pentafluorosulfanylbenzoic acid (1.0 g) was dissolved in methylene chloride (60 ml). Thionyl chloride (5 ml) was added with stirring and the mixture was stirred at RT for 2 h. To complete the reaction, it was subsequently heated at reflux for 3 h. After cooling, the solvent was stripped off, and the residue was dissolved in methylene chloride (50 ml), treated with N,O-dimethylhydroxylamine hydrochloride and Hünig's base (1 ml) was added. After stirring for one hour, the solvent was stripped off, and the residue was taken up with ethyl acetate and washed 5 times with water. The organic phase was dried with magnesium sulfate, filtered and concentrated. 980 mg of the title compound were obtained, which were reacted directly in the next stage.

LCMS-Rt: 1.53 min [M+H$^+$]: 335.0

11d) 1-(3-Dimethylamino-5-pentafluorosulfanylphenyl)ethanone

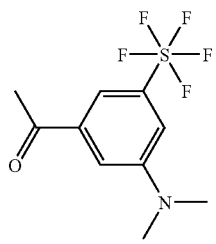

3-Dimethylamino-N-methoxy-N-methyl-5-pentafluorosulfanylbenzamide (980 mg) was dissolved in abs. THF (50 ml) and methylmagnesium bromide solution (2.1 ml; 3 M solution in diethyl ether) was added dropwise at 0° C. with stirring. After addition was completed, the ice bath was removed and the mixture was stirred at RT for 1 h. To complete the reaction, more methylmagnesium bromide solution (0.3 ml) was added and the mixture was stirred for a further 2 h. After storage overnight in a refrigerator, the reaction mixture was treated with 1 N hydrochloric acid with cooling. After addition of water and ethyl acetate, it was extracted a further two times with ethyl acetate, and the combined organic phases were dried with magnesium sulfate, filtered and concentrated. The residue was purified by means of chromatography on silica gel (n-heptane/ethyl acetate 100/0 to 50/50 in 30 min). The product-containing fractions were combined, the solvent was removed and the residue was dried in a high vacuum. 650 mg of the title compound were obtained.

LCMS-Rt: 1.69 min [M+H$^+$]: 290.0

11e) [3-(1,1-Dimethoxyethyl)-5-pentafluorosulfanylphenyl]dimethylamine

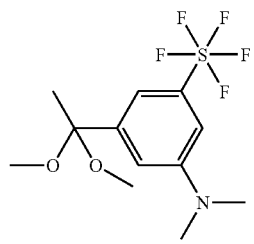

1-(3-Dimethylamino-5-pentafluorosulfanyl phenyl)ethanone (650 mg) was dissolved in methanol (50 ml) and treated with stirring with trimethyl orthoformate (715 mg) and DL-10-camphorsulfonic acid (10 mg). After stirring for 3 h, more orthoformate (200 mg) was added, and the mixture was stirred for 2 h and then allowed to stand overnight. The solvent was then stripped off and the residue was dried in a high vacuum. 730 mg of crude product were obtained, which were reacted directly in the next stage.

$^1$H-NMR (400 MHz, DMSO-d$_6$) [ppm]: 7.01 (1H); 6.79 (1H); 6.93 (1H); 3.10 (6H); 2.98 (6H); 1.47 (3H)

11f) [3-(2-Bromo-1,1-dimethoxyethyl)-5-pentafluorosulfanylphenyl]dimethylamine and [3-(2-bromo-1,1-dimethoxyethyl)-5-pentafluorosulfanylphenyl]methylamine

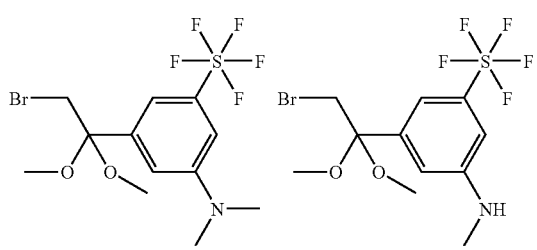

[3-(1,1-Dimethoxyethyl)-5-pentafluorosulfanylphenyl]dimethylamine (730 mg) was dissolved in a mixture of methanol (15 ml) and THF (15 ml). Phenyltrimethyl tribromide (818 mg) was added to this with stirring. After 3 h, more phenyltrimethyl tribromide (205 mg) was added to complete the reaction and the mixture was stirred at 60° C. for 2 h. After standing overnight, sodium thiosulfate solution, water and ethyl acetate were added. The aqueous phase was extracted a further three times with ethyl acetate. The combined extracts were dried with magnesium sulfate, filtered and concentrated. The residue was purified by means of chromatography on silica gel (n-heptane/ethyl acetate 100/0 to 50/50 in 30 min). The product-containing fractions were combined, the solvent was removed and the residue was dried in a high vacuum.

490 mg of the dimethylamino compound and 144 mg of the monomethylamino compound were obtained.

Dimethylamine Derivative:

$^1$H-NMR (500 MHz, DMSO-d$_6$) [ppm]: 7.14 (1H); 7.00 (1H); 6.95 (1H); 3.85 (2H); 3.14 (6H); 2.99 (6H)

Monomethylamine Derivative:

$^1$H-NMR (500 MHz, DMSO-d$_6$) [ppm]: 7.02 (1H); 6.91 (1H); 6.84 (1H); 6.34 (1H); 3.80 (2H); 3.14 (6H); 2.71 (3H)

11g) 2-Bromo-1-(3-dimethylamino-5-pentafluorosulfanylphenyl)ethanone

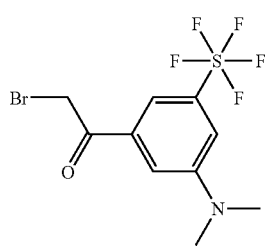

[3-(2-Bromo-1,1-dimethoxyethyl)-5-pentafluorosulfanylphenyl]dimethylamine (230 mg) was suspended in water (2.3 ml) and then concentrated sulfuric acid (2.3 ml) was added dropwise with cooling. After stirring at RT for 2 h, the mixture was diluted with water (20 ml) and extracted three times with ethyl acetate. The combined organic phases were washed twice with saturated sodium hydrogencarbonate solution, dried over magnesium sulfate, filtered and concentrated. The residue was dissolved in acetonitrile/water, frozen and freeze-dried overnight. 170 mg of the desired compound were obtained.

LCMS-Rt: 1.80 min [M+H$^+$]: 367.9; 369.9

11h) 1-(3-Dimethylamino-5-pentafluorosulfanylphenyl)-2-(3-iminoimidazo[1,5-a]pyridin-2-yl)ethanone as the trifluoroacetic acid salt Imidazo[1,5-a]pyridin-3-ylamine as the trifluoroacetic acid salt (20 mg, Example 1c) was dissolved in abs. THF (5 ml) and 2-bromo-1-(3-dimethylamino-5-pentafluorosulfanylphenyl)ethanone (29 mg) and Hünig's base (14 μl) were added. After stirring at RT for 6 h and allowing to stand overnight, water was added and the mixture was extracted three times with ethyl acetate. The combined organic phases were dried over magnesium sulfate, filtered and concentrated. The residue was purified by means of preparative HPLC. The product-containing fractions were combined, freed from the acetonitrile and freeze-dried. 18 mg of the desired compound were obtained as the trifluoroacetic acid salt. LCMS-Rt: 1.21 min [M+H$^+$]: 421.0

Example 12

2-[2-(8-tert-Butyl-4-methyl-3,4-dihydro-2H-benzo[1,4]oxazin-6-yl)-2-oxoethyl]-7-ethoxy-3-imino-2,3-dihydroimidazo[1,5-a]pyridine-6-carboxylic acid methylamide as the trifluoroacetic acid salt

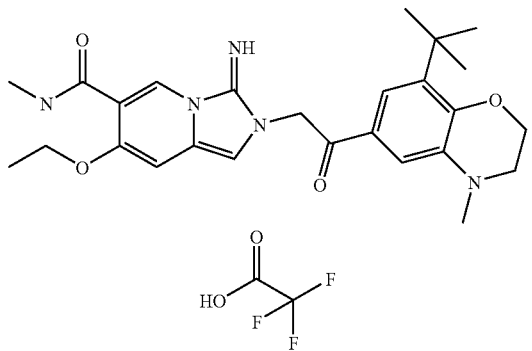

12a) 4-Chloro-6,N-dimethylnicotinamide

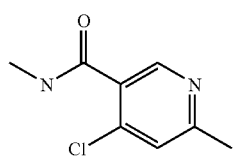

4-Hydroxy-6-methylnicotinic acid (5 g) was dissolved in abs. DCM (30 ml) and treated with 10 drops of DMF. Oxalyl chloride (15 ml) was carefully added dropwise to this mixture. After stirring for four hours and allowing to stand overnight, the solvent was stripped off and for further drying the mixture was attached to the high vacuum. The 4-chloro-6-methylnicotinoyl chloride obtained (8 g) was dissolved in abs. DCM (160 ml). After cooling to 0° C., a 40% strength methanolic methylamine solution (66 ml) was added dropwise in the course of 15 min. After removal of the cooling, the mixture was additionally stirred at RT for 2 h. After addition of water (150 ml), it was extracted with DCM (three times). The combined organic phases were dried over sodium sulfate, filtered and concentrated. 4.4 g of the desired compound were obtained.

LCMS-Rt: 0.34 min [M+H$^+$]: 185.1

12b) 4-Ethoxy-6,N-dimethylnicotinamide

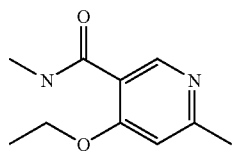

4-Chloro-6,N-dimethylnicotinamide (2.4 g) was dissolved with stirring in abs. ethanol (40 ml) and treated with sodium ethoxide (1.8 g). After stirring at RT for 4 h, the mixture was allowed to stand overnight. After addition of water, it was extracted 3 times with DCM. The combined organic phases were dried over sodium sulfate, filtered and concentrated. 2.2 g of the desired compound were obtained.

LCMS-Rt: 0.32 min [M+H$^+$]: 195.1

12c) 4-Ethoxy-6,N-dimethyl-1-oxynicotinamide

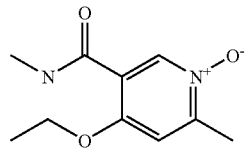

4-Ethoxy-6,N-dimethylnicotinamide (2.2 g) was dissolved in chloroform (160 ml), and treated in portions with meta-chloroperbenzoic acid (2.7 g) with ice cooling and stirring. After removal of the ice bath, the mixture was stirred for 4 h and allowed to stand overnight. After addition of 5% strength sodium carbonate solution, it was extracted three times with chloroform. The combined organic phases were dried over sodium sulfate, filtered and concentrated, so that 979 mg of crude product were obtained. This was chromatographed on silica gel (DCM/MeOH gradient). The product-containing fractions were combined and brought to dryness. 717 mg of the compound sought were obtained.

The aqueous phase was freeze-dried overnight and the residue was stirred with DCM. After filtration, it was brought to dryness. The residue corresponded to a further 720 mg of the desired product.

LCMS-Rt: 0.52 min [M+H$^+$]: 211.1

12d)
4-Ethoxy-6-hydroxymethyl-N-methylnicotinamide
as the trifluoroacetic acid salt

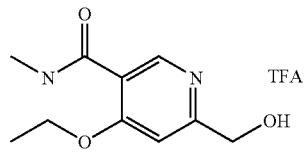

4-Ethoxy-6,N-dimethyl-1-oxynicotinamide (720 mg) was dissolved in abs. DCM (45 ml) with stirring and treated with trifluoroacetic anhydride (4.8 ml). After stirring at RT, the mixture was allowed to stand overnight and subsequently 75% of the solvent was stripped off. The residue was treated with saturated sodium chloride solution and adjusted to pH 9 with potassium carbonate. After extracting with DCM (three times) it was dried over sodium sulfate, filtered and concentrated. The crude product was purified by means of preparative HPLC. The product-containing fractions were combined, freed from the acetonitrile and freeze-dried. 696 mg of the desired compound were obtained.

LCMS-Rt: 0.25 min [M+H$^+$]: 211.1

12e)
4-Ethoxy-5-methylcarbamoylpyridin-2-ylmethyl
methanesulfonate

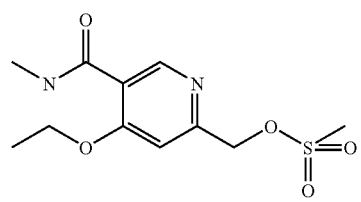

4-Ethoxy-6-hydroxymethyl-N-methylnicotinamide (696 mg as the trifluoroacetic acid salt) was taken up in a little DCM, treated with saturated common salt solution and adjusted to pH 9 with solid potassium carbonate. After extraction with DCM (three times), the combined organic phases were dried over sodium sulfate, filtered and concentrated. 445 mg of the TFA-free compound were obtained. These were dissolved in absolute CM (30 ml) and treated successively with methanesulfonic anhydride (1.3 g dissolved in 5 ml of abs. DCM) and triethylamine (1.44 ml). After 2 h, water and saturated common salt solution were added. After extraction with DCM (3 times), the combined organic phases were dried over sodium sulfate, filtered and concentrated. For the removal of the triethylamine to the greatest possible extent, the residue was extracted again in the presence of 10% strength citric acid. 485 mg of the desired compound were obtained.

LCMS-Rt: 0.72 min [M+H$^+$]: 289.0

12f) 6-Aminomethyl-4-ethoxy-N-methylnicotinamide

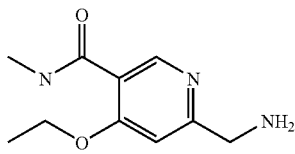

4-Ethoxy-5-methylcarbamoylpyridin-2-ylmethyl methanesulfonate (436 mg), dissolved in abs. MeOH (7 ml), was added dropwise to a methanolic ammonia solution (7.1 ml; 7N) in a microwave vessel at RT and with stirring in the course of 10 min. After standing overnight, the solvent was stripped off and the residue was purified by means of preparative HPLC. The product-containing fractions were combined, freed from the acetonitrile and freeze-dried. The product was treated with saturated sodium chloride solution and rendered alkaline with potassium carbonate. After extraction with methylene chloride, the combined organic phases were dried with sodium sulfate, filtered and concentrated. 71 mg of the title compound were obtained.

LCMS-Rt: 0.27 min [M+H$^+$]: 210.1

12g) 3-Amino-7-ethoxyimidazo[1,5-a]pyridine-6-carboxylic acid methylamide as the trifluoroacetic acid salt

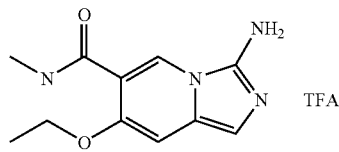

6-Aminomethyl-4-ethoxy-N-methylnicotinamide (68 mg) was initially introduced dissolved in abs. toluene (10 ml). The mixture was then treated dropwise with cyanogen bromide (48 mg), dissolved in abs. toluene (1 ml), at RT with stirring and under an argon atmosphere. After stirring at RT for four h, the solvent was removed under reduced pressure, the residue was stirred with methylene chloride and the insoluble matter was filtered off. The filtrate was brought to dryness and subsequently purified by means of preparative HPLC. The filter residue was again extracted with methylene chloride and the residue obtained after filtration was likewise purified by means of preparative HPLC. The product-containing fractions were combined and the acetonitrile was stripped off under reduced pressure. After freeze-drying, 15 mg of the title compound were obtained in addition to 21 mg of starting material.

LCMS-Rt: 0.69 min [M+H$^+$]: 235.0

12h) 2-Bromo-1-(8-tert-butyl-4-methyl-3,4-dihydro-2H-benzo[1,4]oxazin-6-yl)ethanone

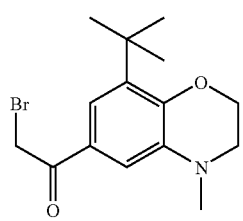

1-(8-tert-Butyl-4-methyl-3,4-dihydro-2H-benzo[1,4]oxazin-6-yl)ethanone (250 mg, purchased from Chembiotek, India) was warmed to 50° C. to 55° C. in a mixture of acetic acid (4 ml) and toluene (8 ml). Bromine (200 mg dissolved in acetic acid) was carefully added dropwise at this temperature. After 2.5 h, the heating was removed, and the mixture was treated with ice water at RT and extracted three times with toluene. The combined organic phases were dried over sodium sulfate, filtered and concentrated. The crude product was purified on silica gel, so that 65 mg of the desired compound were obtained, in addition to a further 43 mg of product, which were slightly contaminated, and 37 mg of starting material.

LCMS-Rt: 1.81 min [M+H$^+$]: 326.0; 328.0

12i) 2-[2-(8-tert-Butyl-4-methyl-3,4-dihydro-2H-benzo[1,4]oxazin-6-yl)-2-oxoethyl]-7-ethoxy-3-imino-2,3-dihydroimidazo[1,5-a]pyridine-6-carboxylic acid methylamide as the trifluoroacetic acid salt 3-Amino-7-ethoxyimidazo[1,5-a]pyridine-6-carboxylic acid methylamide as the trifluoroacetic acid salt (12 mg) was treated with Hünig's base (6.3 µl) in abs. DMF (3 ml) with stirring and under argon. Subsequently, 2-bromo-1-(8-tert-butyl-4-methyl-3,4-dihydro-2H-benzo[1,4]oxazin-6-yl) ethanone (12.5 mg) dissolved in abs. DMF (0.5 ml) was added dropwise to the solution. After stirring at RT for 2.5 h, the mixture was warmed at 40° C. for 30 min and subsequently allowed to stand overnight. The solvent was then removed in a high vacuum and the residue was purified by means of preparative HPLC. The product-containing fractions were combined and the acetonitrile was stripped off under reduced pressure. After freeze-drying, 10 mg of the title compound were obtained.

LCMS-Rt: 1.24 min [M+H$^+$]: 480.2

Example 13

2-[2-(3-tert-Butyl-4-methoxy-5-morpholin-4-ylphenyl)-2-oxoethyl]-7-chloro-3-imino-2,3-dihydroimidazo[1,5-a]pyridine-6-carboxylic acid methylamide as the trifluoroacetic acid salt

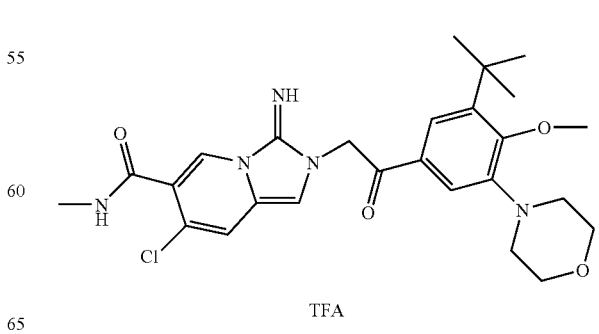

13a) 3-Amino-7-chloroimidazo[1,5-a]pyridine-6-carboxylic acid methylamide as the trifluoroacetic acid salt

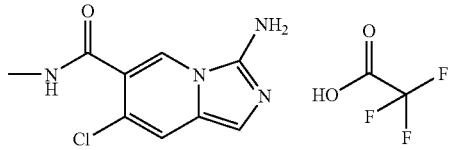

3-Amino-7-chloroimidazo[1,5-a]pyridine-6-carboxylic acid methylamide was synthesized analogously to Example 12a-g), step 12b) being left out. 9 mg of the title compound were obtained.
LCMS-Rt: 0.32 min [M+H$^+$]: 225.0

13b) 2-[2-(3-tert-Butyl-4-methoxy-5-morpholin-4-yl phenyl)-2-oxoethyl]-7-chloro-3-imino-2,3-dihydroimidazo[1,5-a]pyridine-6-carboxylic acid methylamide as the trifluoroacetic acid salt Analogously to the method described in Example 12, 3-amino-7-chloroimidazo[1,5-a]pyridine-6-carboxylic acid methylamide (9 mg as the TFA salt) was coupled with 2-bromo-1-(3-tert-butyl-4-methoxy-5-morpholin-4-ylphenyl)ethanone (10 mg, prepared according to WO 2004/078721) in the presence of Hünig's base. 4 mg of the title compound were obtained.
LCMS-Rt: 1.24 min [M+H$^+$]: 514.2

Example 14

2,2,2-Trifluoro-N-{3-[2-(3-iminoimidazo[1,5-a]pyridin-2-yl)acetyl]-5-pentafluorosulfanylphenyl}acetamide as the trifluoroacetic acid salt

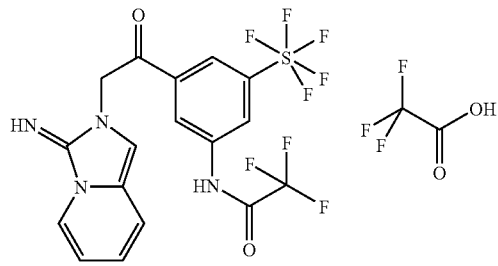

14a) 3-Amino-N-methoxy-N-methyl-5-pentafluorosulfanylbenzamide

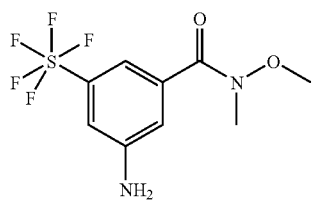

3-Amino-5-pentafluorosulfanylbenzoic acid (200 mg, Example 11a) was dissolved in methylene chloride (12 ml). The following were added successively with stirring: N,O-dimethylhydroxylamine×HCl (148 mg), 1-propanephosphoric anhydride (242 mg) and triethylamine (292 µl). The clear solution was stirred at RT for 4 h and allowed to stand over the weekend. For work-up, the reaction mixture was concentrated, and the residue was taken up in ethyl acetate and extracted twice with potassium hydrogensulfate solution. After the ethyl acetate phase had subsequently been extracted twice with sodium carbonate solution, it was dried over magnesium sulfate, filtered and concentrated. The crude product obtained was purified by means of preparative chromatography. The product-containing fractions were combined, freed from the acetonitrile, rendered basic with saturated sodium hydrogencarbonate solution and extracted with ethyl acetate three times. The combined extracts were dried over magnesium sulfate, filtered and concentrated. 77 mg of the desired compound were obtained.
LCMS-Rt: 1.30 min [M+H$^+$]: 307.0

14b) N-Methoxy-N-methyl-5-pentafluorosulfanyl-3-(2,2,2-trifluoroacetylamino)-benzamide

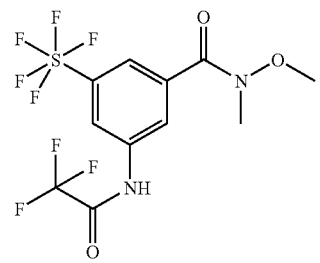

3-Amino-N-methoxy-N-methyl-5-pentafluorosulfanylbenzamide (77 mg) was dissolved in methylene chloride (3 ml) and triethylamine (42 µl) followed by trifluoroacetic anhydride (45 µl) was added with stirring with exclusion of moisture. After stirring at RT for 3 h and standing overnight, water and saturated sodium hydrogencarbonate solution were added, the phases were separated and the methylene chloride phase was additionally washed three times with water, dried over magnesium sulfate, filtered and concentrated. The product obtained (86 mg) was employed without further purification in the next stage.
LCMS-Rt: 1.53 min [M+H$^+$]: 403.0

14c) N-(3-Acetyl-5-pentafluorosulfanylphenyl)-2,2,2-trifluoroacetamide

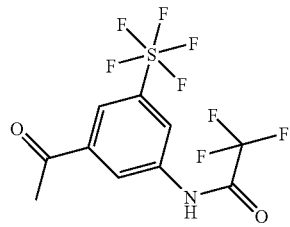

N-Methoxy-N-methyl-5-pentafluorosulfanyl-3-(2,2,2-trifluoroacetylamino)benzamide (20 mg) was dissolved in absolute THF (2 ml) and stirred at RT with lithium hexamethyldisilazane solution (45 µl, 1 M in THF) for 30 min. Methylmagnesium bromide solution (17 µl, 3 M in diethyl ether) was then added dropwise with stirring at 0° C. After stirring at RT for 1 h, 1N hydrochloric acid was added dropwise with cooling, followed by water and ethyl acetate. The organic phase was separated off and the water phase was additionally extracted twice with ethyl acetate. The combined ethyl acetate phases were dried over magnesium sulfate, filtered and concentrated. 17 mg of crude product were obtained. After further N-methoxy-N-methyl-5-pentafluorosulfanyl-3-(2,2,2-trifluoroacetylamino)benzamide (60 mg) was reacted in the manner described (crude product obtained: 60 mg), the crude products were combined and purified by means of preparative chromatography. The product-containing fractions were combined, freed from the acetonitrile, rendered basic with saturated sodium hydrogencarbonate solution and extracted three times with ethyl acetate. The combined extracts were dried over magnesium sulfate, filtered and concentrated. 37 mg of the desired compound were obtained.

LCMS-Rt: 1.61 min [M+H$^+$]: 358.0

14d) N-[3-(2-Bromoacetyl)-5-pentafluorosulfanylphenyl]-2,2,2-trifluoroacetamide

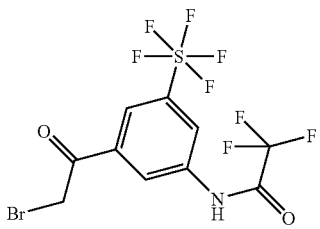

N-(3-Acetyl-5-pentafluorosulfanylphenyl)-2,2,2-trifluoroacetamide (20 mg) was initially introduced dissolved in glacial acetic acid (1 ml), and bromine (9 mg) dissolved in glacial acetic acid (90 µl) was slowly added dropwise. After stirring at RT for 30 min, the mixture was warmed at 60° C. for 1 h. After cooling to RT, the glacial acetic acid was diluted with a large quantity of water and extracted three times with ethyl acetate. The combined extracts were washed with sodium hydrogencarbonate solution until acid-free, dried over magnesium sulfate, filtered and concentrated. The crude product obtained (24 mg) was employed in the next stage without further purification.

$^1$H-NMR (400 MHz, CDCl$_3$) [ppm]: 8.45 [1H], 8.35 [1H], 8.25 [1H], 4.45 [s, 2H]

14e) 2,2,2-Trifluoro-N-{3-[2-(3-iminoimidazo[1,5-a]pyridin-2-yl)acetyl]-5-pentafluorosulfanylphenyl}acetamide as the trifluoroacetic acid salt Imidazo[1,5-a]pyridin-3-ylamine trifluoroacetate (20 mg, Example 1c) was dissolved in absolute THF (4 ml) and N-[3-(2-bromoacetyl)-5-pentafluorosulfanylphenyl]-2,2,2-trifluoroacetamide (26 mg) was added with stirring. After addition of DIPEA (10 µl), the mixture was stirred at RT for 1 h and allowed to stand overnight. After this, the reaction mixture was treated with water, extracted three times with ethyl acetate and the combined ethyl acetate phases were dried with magnesium sulfate, filtered and concentrated. The oily residue was purified by means of preparative chromatography. The product-containing fractions were combined, freed from the acetonitrile and freeze-dried. 7 mg of the desired compound were obtained.

LCMS-Rt: 1.22 min [M+H$^+$]: 489.0

Example 15

1-(3-Bromo-4-methoxy-5-trifluoromethylphenyl)-2-(3-iminoimidazo[1,5-a]pyridin-2-yl)-ethanone as the trifluoroacetic acid salt

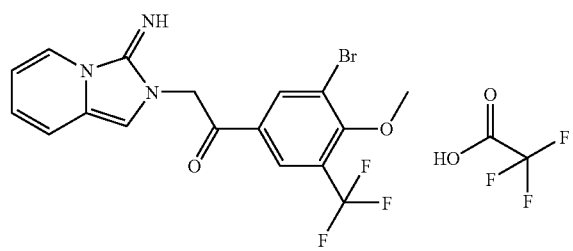

15a) 2-Bromo-1-(3-bromo-4-methoxy-5-trifluoromethylphenyl)ethanone

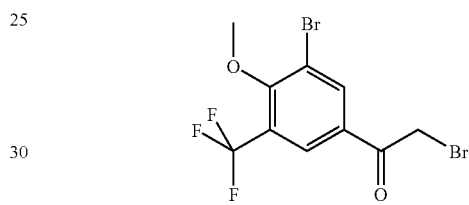

A mixture of water (0.4 ml) and concentrated sulfuric acid (0.4 ml) was initially introduced and 4-methoxy-3-trifluoromethylacetophenone (100 mg) was added at RT. Subsequently, potassium bromate (77 mg) was introduced in portions with stirring. After stirring for 4 h, the reaction mixture was placed in the deep freeze overnight. It was then treated with water and ethyl acetate and the aqueous phase was extracted three times with ethyl acetate. The combined ethyl acetate phases were dried over magnesium sulfate, filtered and concentrated. The crude product was prepurified on silica gel (n-heptane/ethyl acetate gradient) and subsequently finally purified by means of preparative chromatography. The product-containing fractions were combined, freed from the acetonitrile and extracted three times with ethyl acetate. The combined extracts were dried over magnesium sulfate, filtered and concentrated. 12 mg of the desired compound were obtained.

LCMS-Rt: 1.74 min [M+H$^+$]: 374.8 (50%), 376.9 (100%), 378.8 (45%)

15b) 1-(3-Bromo-4-methoxy-5-trifluoromethylphenyl)-2-(3-iminoimidazo[1,5-a]pyridin-2-yl)ethanone as the trifluoroacetic acid salt Imidazo[1,5-a]pyridin-3-ylamine trifluoroacetate (8 mg, Example 1c) was initially introduced in absolute DMF (0.5 ml) at RT together with Hünig's base (5.5 µl). 2-Bromo-1-(3-bromo-4-methoxy-5-trifluoromethylphenyl)ethanone (12 mg, dissolved in 0.5 ml of absolute DMF) was added dropwise with stirring. After stirring at RT for 3.5 h, the solvent was stripped off and the residue was purified by means of preparative chromatography. The product-containing fractions were combined, freed from the acetonitrile and freeze-dried. 4 mg of the desired compound were obtained.

LCMS-Rt: 1.21 min [M+H$^+$]: 428.0; 430.0

Example 16

2-(3-Iminoimidazo[1,5-a]pyridin-2-yl)-1-(4-methoxy-3-morpholin-4-yl-5-trifluoromethylphenyl)ethanone as the trifluoroacetic acid salt

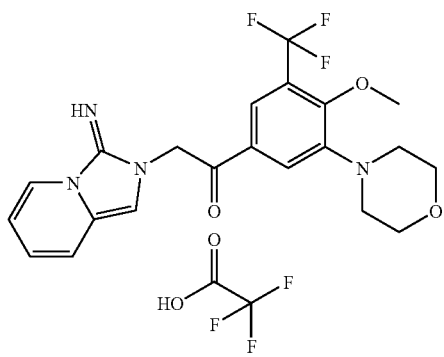

16a) 1-(3-Bromo-4-hydroxy-5-trifluoromethylphenyl)ethanone

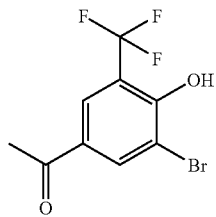

4-Hydroxy-3-(trifluoromethyl)acetophenone (4 g) was initially introduced in acetonitrile (150 ml) and N-bromosuccinimide (4.5 g, dissolved in 100 ml acetonitrile) was added dropwise at −10° C. After addition was complete, the cooling bath was removed and the mixture was stirred for 5 h. After standing overnight, the volume of solvent was reduced to a quarter and the residue was treated with n-heptane/water. After separating off the organic phase, this was washed once with 5% strength sodium thiosulfate solution and once with water. The precipitate formed in the course of this (6.9 g) was filtered off with suction and directly reacted further in the next stage.

$^1$H-NMR (500 MHz, DMSO-d$_6$) [ppm]: 11.3 [br, 1H], 8.37 [1H], 8.06 [1H], 2.57 [s, 3H]

16b) 1-Bromo-5-(1,1-dimethoxyethyl)-2-methoxy-3-trifluoromethylbenzene

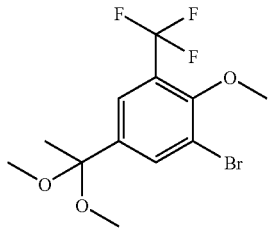

1-(3-Bromo-4-hydroxy-5-trifluoromethylphenyl)ethanone (6.8 g) was dissolved in absolute methanol (50 ml) and treated successively with DL-10-camphorsulfonic acid (111 mg) and trimethyl orthoformate (8 ml). After stirring at RT for 2 h, DMF (75 ml) and potassium carbonate (5.0 g) were added, followed by iodomethane (3 ml). After stirring for 6 h, the batch was allowed to stand overnight and was treated with a 1:1 mixture of n-heptane/water. After separating off the organic phase, it was additionally extracted once with n-heptane and then the combined heptane phases were dried over magnesium sulfate, filtered and concentrated. 7 g of the desired product were obtained.

$^1$H-NMR (500 MHz, DMSO-d$_6$) [ppm]: 7.92 [1H], 7.64 [1H], 3.90 [s, 3H], 3.09 [s, 6H], 1.50 [s, 3H]

16c) 4-[5-(1,1-Dimethoxyethyl)-2-methoxy-3-trifluoromethylphenyl]morpholine

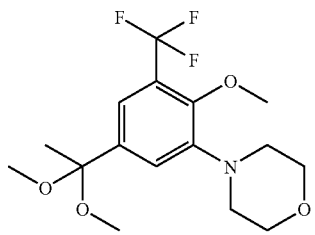

1-Bromo-5-(1,1-dimethoxyethyl)-2-methoxy-3-trifluoromethylbenzene (2 g) was initially introduced and argon was passed through with stirring for 0.5 h. Subsequently, the mixture was treated with Pd(II) acetate (13 mg), BINAP (54 mg) and sodium tertiary-butylate (784 mg), followed by morpholine (0.6 ml). The mixture obtained was stirred under argon at 85° C. for 8 h and after standing overnight at RT it was stirred at 85° C. for a further 8 h and allowed to stand overnight. The solvent was then stripped off and the residue was purified on silica gel (n-heptane-ethyl acetate gradient). 468 mg of the desired product were obtained.

$^1$H-NMR (500 MHz, DMSO-d$_6$) [ppm]: 7.26 [1H], 7.23 [1H], 3.88 [s, 3H], 3.78 [m, 4H], 3.10 [s, 6H], 3.06 [m, 4H], 1.47 [s, 3H]

16d) 2-Bromo-1-(4-methoxy-3-morpholin-4-yl-5-trifluoromethylphenyl)ethanone

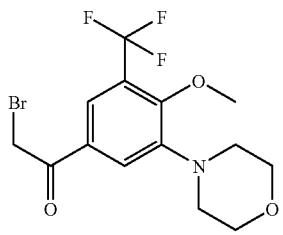

4-[5-(1,1-Dimethoxyethyl)-2-methoxy-3-trifluoromethylphenyl]morpholine (460 mg) was initially introduced in absolute THF (4 ml) and methanol (1.6 ml), and phenyltrimethylammonium bromide (530 mg) was added with stirring at 7° C. The cooling bath was then removed and the mixture was stirred for 8 h. After standing overnight, it was treated with 5% strength sodium thiosulfate solution (0.8 ml) and water (4 ml). The aqueous phase was extracted three times with ethyl acetate and the combined ethyl acetate extracts were dried over magnesium sulfate, filtered and concentrated. The residue was dissolved in acetonitrile (15 ml) and treated with a mixture (5 ml) of acetonitrile (90 parts), water (10) and TFA (0.05) and further TFA (0.5 ml). This mixture was stirred at RT for approximately 4 h. The solvent was then stripped off and the residue was treated with water, neutralized with saturated sodium hydrogencarbonate solution, extracted three times with ethyl acetate and the combined ethyl acetate phases were dried over magnesium sulfate, filtered and concentrated. The residue was purified on silica gel (n-heptane-ethyl acetate gradient). After combination of the product-containing fractions, the mixture was brought to dryness. 200 mg of the desired compound were obtained.

LCMS-Rt: 1.67 min [M+H$^+$]: 382.0; 384.0

16e) 2-(3-Iminoimidazo[1,5-a]pyridin-2-yl)-1-(4-methoxy-3-morpholin-4-yl-5-trifluoromethylphenyl)ethanone as the trifluoroacetic acid salt Imidazo[1,5-a]pyridin-3-ylamine trifluoroacetate (30 mg, Example 1c) was dissolved in absolute DMF (4 ml) with stirring and DIPEA (20 µl) was added. After 2-bromo-1-(4-methoxy-3-morpholin-4-yl-5-trifluoromethylphenyl)ethanone (51 mg, dissolved in 1 ml of DMF) had been slowly added dropwise in the course of 15 min, the mixture was stirred at RT for 3.5 h. After standing overnight, the solvent was stripped off and the residue was purified by means of preparative chromatography. The product-containing fractions were combined, freed from the acetonitrile and freeze-dried. 35 mg of the desired compound were obtained.

LCMS-Rt: 1.17 min [M+H$^+$]: 435.1

Example 17

6-Ethoxy-3-imino-2-[2-(3-methylamino-5-pentafluorosulfanylphenyl)-2-oxoethyl]-2,3-dihydro-1H-imidazo[1,5-a]pyridin-5-one as the trifluoroacetic acid salt

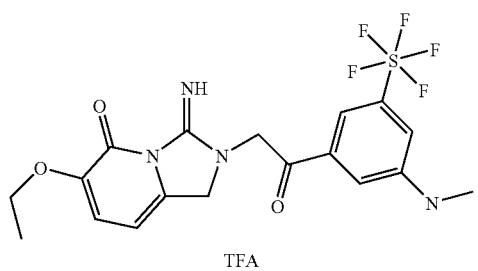

17a) 3-Ethoxy-2-fluoro-6-methylpyridine

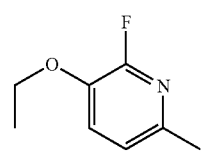

2-Fluoro-3-hydroxy-6-picoline (500 mg) was initially introduced in absolute DMF (20 ml) and potassium carbonate (1 g) was added. After this, ethyl iodide (0.6 ml) was added dropwise with stirring and the mixture was stirred for 1 h. Subsequently, water and ethyl acetate were added to the reaction mixture. After separating off the organic phase, the mixture was additionally extracted three times with ethyl acetate. The combined extracts were dried over sodium sulfate, filtered and concentrated. The crude product obtained (477 mg) was reacted directly in the next stage.

$^1$H-NMR (500 MHz, DMSO-d$_6$) [ppm]: 7.52 [dd, 1H], 7.10 [d, 1H], 4.10 [q, 2H], 2.32 [s, 3H], 1.33 [t, 3H]

17b) 6-Bromomethyl-3-ethoxy-2-fluoropyridine

3-Ethoxy-2-fluoro-6-methylpyridine (400 mg) was initially introduced in carbon tetrachloride (30 ml) and, after addition of N-bromosuccinimide (505 mg) and 2,2'-azobis(2-methylpropionitrile) (85 mg), the reaction mixture was heated at reflux for 7 h. After standing overnight at RT, it was treated with water and extracted three times with dichloromethane. The combined organic phases were dried over sodium sulfate, filtered and concentrated. The residue was purified on silica gel (n-heptane-ethyl acetate gradient). After the combination of the product-containing fractions, it was brought to dryness. 393 mg of the desired compound were obtained.

LCMS-Rt: 1.40 min [M+H$^+$]: 233.9; 235.9

17c) C-(5-Ethoxy-6-fluoropyridin-2-yl)methylamine as the trifluoroacetic acid salt

6-Bromomethyl-3-ethoxy-2-fluoropyridine (390 mg) was dissolved in chloroform (50 ml) and treated with hexamethylenetetramine (234 mg) with stirring. After stirring at 50° C. for 1 h, the solvent was removed and the residue was taken up with absolute ethanol (35 ml). After addition of concentrated hydrochloric acid (1 ml), the mixture was stirred at 50° C. for 3 h and then allowed to stand overnight at RT. After stripping off the solvent, the residue was taken up with water and freeze-dried. A part of the crude product was purified by means of preparative chromatography. The product-containing fractions were combined, freed from the acetonitrile and freeze-dried. 134 mg of the desired compound were obtained.

LCMS-Rt: 0.48 min [M+H$^+$]: 171.1

17d)
3-Amino-6-ethoxy-1H-imidazo[1,5-a]pyridin-5-one as the trifluoroacetic acid salt

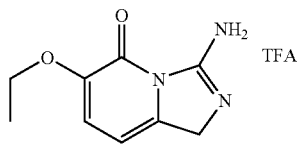

C-(5-Ethoxy-6-fluoropyridin-2-yl)methylamine trifluoroacetate (134 mg) was taken up with a little water, treated with 1.5 ml of saturated sodium chloride solution, rendered alkaline with potassium carbonate (47 mg) and then the aqueous phase was extracted three times with DCM. The combined organic phases were dried over sodium sulfate, filtered and concentrated. The residue was taken up with absolute toluene (8 ml) and dissolved with stirring. The mixture was then treated dropwise with a cyanogen bromide solution (0.18 ml, 5 M in acetonitrile). After 1.5 h, the solvent was removed and the residue was purified by means of preparative chromatography. The product-containing fractions were combined, freed from the acetonitrile and freeze-dried. The freeze-drying with water was repeated three times in the presence of TFA (0.05%). After this, 55 mg of the desired compound were obtained.

LCMS-Rt: 0.31 min [M+H$^+$]: 194.1

17e) 2-Bromo-1-(3-methylamino-5-pentafluorosulfanylphenyl)ethanone

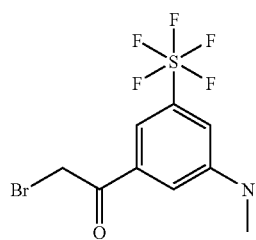

[3-(2-Bromo-1,1-dimethoxyethyl)-5-pentafluorosulfanylphenyl]methylamine (400 mg, prepared as described in Example 11f)) was suspended in water (4 ml) and then concentrated sulfuric acid (4 ml) was added dropwise with stirring and cooling. After stirring at RT for 4 h, the batch was poured onto ice water and carefully adjusted to pH 8 with saturated sodium hydrogencarbonate solution. It was then extracted 3 times with ethyl acetate and the combined extracts were dried over magnesium sulfate, filtered and concentrated. 312 mg of crude product were obtained. 100 mg thereof were purified by means of preparative chromatography. The product-containing fractions were combined, freed from the acetonitrile, rendered basic with saturated sodium hydrogencarbonate solution and extracted three times with ethyl acetate. The combined extracts were dried over magnesium sulfate, filtered and concentrated. 59 mg of the desired compound were obtained.

LCMS-Rt: 1.67 min [M+H$^+$]: 353.9; 355.9

17f) 6-Ethoxy-3-imino-2-[2-(3-methylamino-5-pentafluorosulfanylphenyl)-2-oxoethyl]-2,3-dihydro-1H-imidazo[1,5-a]pyridin-5-one 3-Amino-6-ethoxy-1H-imidazo[1,5-a]pyridin-5-one trifluoroacetic acid salt (25 mg) was dissolved in a little water and rendered alkaline with saturated sodium hydrogencarbonate solution. The aqueous phase was extracted three times with ethyl acetate and the combined extracts were dried over sodium sulfate, filtered and concentrated. 14 mg of the free base were obtained, which was dissolved in DMF (2.5 ml). 2-Bromo-1-(3-methylamino-5-pentafluorosulfanylphenyl) ethanone (26 mg, dissolved in 0.5 ml of DMF) was added dropwise to this solution with stirring in the course of 5 min. The mixture was stirred at RT for 3 h and allowed to stand overnight. The solvent was then removed and the crude product was purified by means of preparative chromatography. The product-containing fractions were combined, freed from the acetonitrile and freeze-dried. 17 mg of the desired compound were obtained.

LCMS-Rt: 1.18 min [M+H$^+$]: 467.0

Example 18

2-[2-(3-tert-Butyl-4-methoxy-5-morpholin-4-ylphenyl)-2-oxoethyl]-6-ethoxy-3-imino-2,3-dihydro-1H-imidazo[1,5-a]pyridin-5-one as the trifluoroacetic acid salt

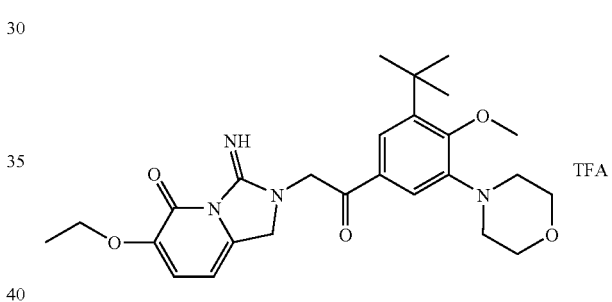

Analogously to Example 17), 3-amino-6-ethoxy-1H-imidazo[1,5-a]pyridin-5-one trifluoroacetic acid salt (25 mg, Example 17) was reacted with 2-bromo-1-(3-tert-butyl-4-methoxy-5-morpholin-4-ylphenylethanone (30 mg, Example 10).

19 mg of the title compound were obtained.

LCMS-Rt: 1.27 min [M+H$^+$]: 483.2

Example 19

2-[2-(3-tert-Butyl-4-methoxy-5-morpholin-4-ylphenyl)-2-oxoethyl]-7-ethoxy-3-imino-2,3-dihydroimidazo[1,5-a]pyridine-6-carboxylic acid Methylamide as the trifluoroacetic acid salt

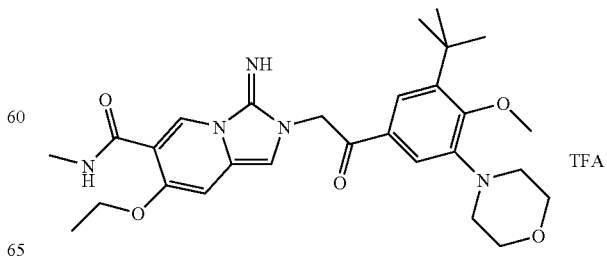

19a) N-(4-Ethoxy-5-methylcarbamoylpyridin-2-ylm-ethyl)-N'-(fluoren-9-ylmethyloxycarbonyl)thiourea

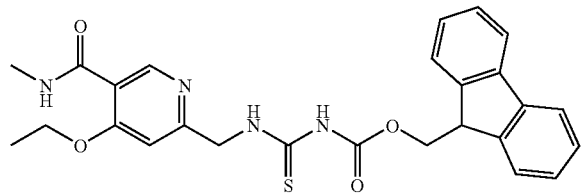

500 mg (2.39 mmol) of 6-aminomethyl-4-ethoxy-N-methylnicotinamide (Example 12f) were dissolved in 25 ml of dioxane and treated at RT with 672.4 mg (2.39 mmol) of fluoren-9-ylmethyloxycarbonyl isothiocyanate. After one hour, the mixture was freed from the solvent and the residue was taken up in DCM. It was washed three times with aqueous LiCl solution and once with water. After drying with $MgSO_4$, the mixture was concentrated and the crude product (875 mg) thus obtained was reacted further without further purification.
LCMS-Rt: 1.31 min [M+H$^+$]: 491.2

19b) 9H-Fluoren-9-ylmethyl (7-ethoxy-6-methylcarbamoyl-2H-imidazo[1,5-a]pyridin-3-ylidene)carbamate

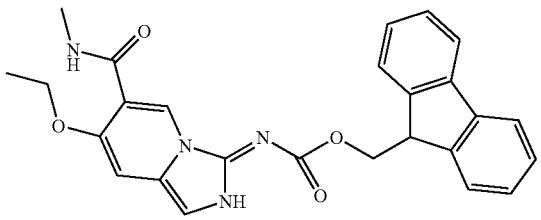

875 mg of N-(4-ethoxy-5-methylcarbamoyl pyridin-2-ylmethyl)-N'-(fluoren-9-ylmethyloxycarbonyl)thiourea (Example 19a, crude product) were dissolved in 25 ml of dioxane and treated at RT with 837 mg (1.96 mmol) of mercury(II) trifluoroacetate. After 10 minutes, the mixture was concentrated and the residue was taken up in DCM. The organic phase was washed three times with 4% strength LiCl solution and once with water, dried with $MgSO_4$ and concentrated in a rotary evaporator. The crude product thus obtained (590 mg) was reacted further without further purification.
LCMS-Rt: 1.25 min [M+H$^+$]: 457.2

19c) 2-[2-(3-tert-Butyl-4-methoxy-5-morpholin-4-ylphenyl)-2-oxoethyl]-7-ethoxy-3-imino-2,3-dihydroimidazo[1,5-a]pyridine-6-carboxylic acid methylamide as the trifluoroacetic acid salt 590 mg of 9H-fluoren-9-ylmethyl (7-ethoxy-6-methylcarbamoyl-2H-imidazo[1,5-a]pyridin-3-ylidene)carbamate (19b, crude product) were dissolved in 25 ml of dimethylacetamide and treated with 573 mg (1.55 mmol) of 2-bromo-1-(3-tert-butyl-4-methoxy-5-morpholin-4-ylphenyl)ethanone (prepared according to WO 2004/078721). The solution was stirred at 70° C. for three hours. After standing overnight at RT, it was stirred for a further two hours at 95° C. The solvent was then separated off and the crude product was purified twice on a preparative HPLC, after which it was possible to isolate 63.5 mg of the title compound.
LCMS-Rt (method B): 1.52 min [M+H$^+$]: 524.2

Example 20

Ethyl 2-[2-(3-tert-butyl-4-methoxy-5-morpholin-4-ylphenyl)-2-oxoethyl]-3-imino-5-methoxy-2,3-dihydroimidazo[1,5-a]pyridine-7-carboxylate as the trifluoroacetic acid salt

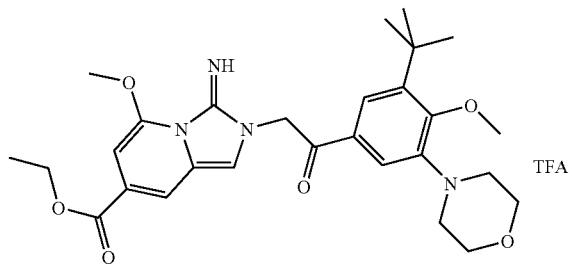

20a) Ethyl 2-hydroxy-6-methylisonicotinate

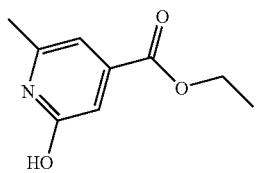

20.0 g (130.6 mmol) of 2-hydroxy-6-methylisonicotinic acid were dissolved in 200 ml of ethanol and treated with 20 ml of concentrated $H_2SO_4$. After the reaction mixture had been refluxed for two hours, it was freed from the solvent. The residue was taken up in saturated $NaHCO_3$ solution and extracted three times with DCM. The combined organic phases were dried with $Na_2SO_4$ and concentrated, 20.1 g of the title compound being isolated.
LCMS-Rt: 0.82 min [M+H$^+$]: 182.2

20b) Ethyl 2-methoxy-6-methylisonicotinate

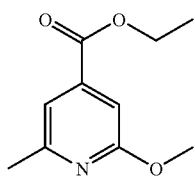

20.0 g (111.4 mmol) of ethyl 2-hydroxy-6-methylisonicotinate (20a) were suspended in 330 ml of toluene. After addition of 36.54 g (132.5 mmol) of $Ag_2CO_3$ and 23.5 g (165.6 mmol) of methyl iodide, the mixture was heated to 100° C. with KPG stirring. After 4 hours, the reaction mixture was allowed to cool to RT and it was filtered through Celite. The filtrate was washed twice with water, dried with $Na_2SO_4$ and concentrated, 16.9 g of the title compound being isolated as a yellowish oil.
LCMS-Rt: 1.49 min [M+H$^+$]: 196.2.

20c) Ethyl 2-bromomethyl-6-methoxyisonicotinate

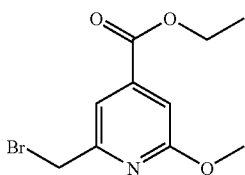

16.9 g (86.6 mmol) of ethyl 2-methoxy-6-methylisonicotinate (19b) were dissolved in carbon tetrachloride and heated to reflux after addition of 16.18 g (90.9 mmol) of N-bromosuccinimide and 0.28 g (1.73 mmol) of AIBN. After reflux for three hours and standing overnight at RT, a further 7.7 g (43.3 mmol) of N-bromosuccinimide were added and the mixture was refluxed for three hours. After cooling to RT, it was diluted with DCM, washed twice with saturated $NaHCO_3$ solution and once with water, dried with $MgSO_4$ and concentrated in a rotary evaporator. The residue was purified on a preparative HPLC. The product fractions were freed from the acetonitrile at reduced pressure and the aqueous solutions were extracted with DCM. The organic phase was dried with $MgSO_4$ and concentrated in a rotary evaporator, 10.95 g of the title compound being isolated.

LCMS-Rt: 1.65 min [M+H$^+$]: 274.1

20d) Ethyl 2-aminomethyl-6-methoxyisonicotinate

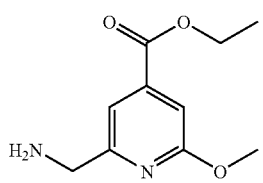

6.72 g (47.9 mmol) of hexamethylenetetramine (urotropin) were initially introduced in 250 ml of chloroform and a solution of 10.95 g (39.95 mmol) of ethyl 2-bromomethyl-6-methoxyisonicotinate (20c) in chloroform was added dropwise at 0° C. The mixture was stirred at RT for 4.5 hours and after this a further 3.36 g (24.0 mmol) of hexamethylenetetramine (urotropin) was added. After standing at RT for a further 60 hours, the solvent was distilled off under reduced pressure and the residue was dissolved in 500 ml of ethanol. 50 ml of concentrated HCl were added and the mixture was stirred at RT for two hours. After addition of a further 30 ml of concentrated HCl and stirring at RT overnight, it was freed from the solvent under reduced pressure. The residue was taken up in DCM and carefully treated with $K_2CO_3$ until evolution of gas was no longer observed. Subsequently, it was washed twice with saturated $K_2CO_3$ solution, and the organic phase was dried with $MgSO_4$ and concentrated. The crude product thus obtained (7.60 g) was reacted further without further purification. LCMS-Rt: 0.74 min [M+H$^+$]: 211.2

20e) N-(4-Ethoxycarbonyl-6-methoxypyridin-2-ylmethyl)-N'-(fluoren-9-ylmethyloxycarbonyl)thiourea

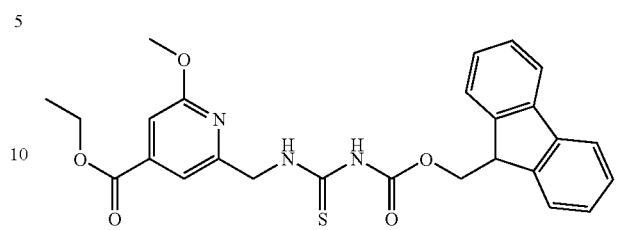

6.67 g (31.7 mmol) of ethyl 2-aminomethyl-6-methoxyisonicotinate (20d) were dissolved in 175 ml of toluene and treated at RT with 8.93 g (281.3 mmol) of fluoren-9-ylmethyloxycarbonyl isothiocyanate. After 15 minutes, the resulting precipitate was filtered off and dried at 50° C., 4.6 g of the title compound being isolated. The filtrate was concentrated, and the residue was taken up in DCM and washed three times with water. The organic phase was dried with $MgSO_4$ and concentrated. The crude product thus obtained was chromatographed on silica gel (heptane/ethyl acetate 90:10→75:25), it being possible to isolate a further 8.1 g of the title compound.

LCMS-Rt: 2.21 min [M+H$^+$]: 492.0

20f) Ethyl 3-imino-5-methoxy-2,3-dihydroimidazo[1,5-a]pyridine-7-carboxylate

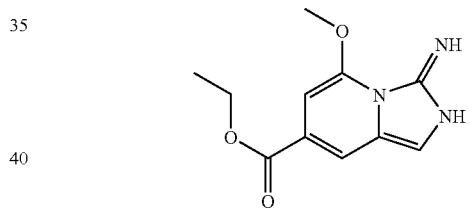

1.17 g (2.38 mmol) of N-(4-ethoxycarbonyl-6-methoxypyridin-2-ylmethyl)-N'-(fluoren-9-ylmethyloxycarbonyl)thiourea (20e) were treated with 491 mg (2.38 mmol) of DCC in 25 ml of toluene and refluxed for six hours. After standing overnight at RT, the mixture was freed from the solvent and the residue was chromatographed on silica gel (heptane/ethyl acetate 75:25→ethyl acetate/methanol 90:10), it being possible to isolate 88 mg of the title compound.

LCMS-Rt: 0.81 min [M+H$^+$]: 236.2

20g) Ethyl 2-[2-(3-tert-butyl-4-methoxy-5-morpholin-4-ylphenyl)-2-oxoethyl]-3-imino-5-methoxy-2,3-dihydroimidazo[1,5-a]pyridine-7-carboxylate as the trifluoroacetic acid salt 88 mg (0.37 mmol) of ethyl 3-imino-5-methoxy-2,3-dihydroimidazo[1,5-a]pyridine-7-carboxylate (20f) were dissolved in 4 ml of dimethylacetamide and treated with a solution of 138.5 mg (0.37 mmol) of 2-bromo-1-(3-tert-butyl-4-methoxy-5-morpholin-4-ylphenyl)ethanone (prepared according to WO 2004/078721) in 2 ml of dimethylacetamide. After 24 hours at RT, the mixture was freed from the solvent under reduced pressure and the residue was purified on a preparative HPLC, it being possible to isolate 61 mg of the title compound.

LCMS-Rt (method B): 1.66 min [M+H$^+$]: 525.3

Pharmacological Examples

PAR 1 determination method: Inhibition of PAR1-mediated platelet aggregation The pharmacological testing of the substances was carried out in the platelet aggregation induced by TRAP (thrombin-receptor activating peptide) in a 96-well format. To this end, blood from healthy volunteers was taken in 20 ml syringes into which 2 ml of 3.13% strength sodium citrate solution was initially introduced. After a 20-minute centrifugation at 150×g, the platelet-rich plasma (PRP) was separated off and treated with 1 µl of PGE1 solution (500 µg/ml in ethanol)/ml of PRP. After incubation at RT for 5 minutes, this was centrifuged at 120×g for 15 minutes in order to remove the leucocytes. The leucocyte-free PRP was transferred to 15 ml PP tubes in 5 ml portions and centrifuged off at 360×g for 15 minutes in order to pellet the platelets. Subsequently, the plasma was decanted and the platelet sediment from 5 ml of PRP was resuspended in 1 ml of Tyrode (120 mM NaCl, 2.6 mM KCl, 12 mM NaHCO$_3$, 0.39 mM NaH$_2$PO$_4$×H$_2$O, 10 mM HEPES, 0.35% BSA, 5.5 mM glucose, pH 7.4) and adjusted with Tyrode to a platelet count of 3×10$^5$/microliter (µl). 13 ml of this cell suspension were then treated with 866 µl of 10 mM CaCl$_2$ solution and 120 µl thereof per well were pipetted to a 96-well plate, in which 15 µl of the substance to be tested were initially introduced. After incubation in the dark at RT for 30 minutes, 15 µl of a TRAP solution (70-100 µM) were added as the agonist and kinetics were recorded with shaking at 37° C. for 20 minutes in a SpectraMax 340 at 650 nm. The areas under the curves of negative control (Tyrode/DMSO) and positive control (15 µl of agonist/DMSO) were calculated and the difference was defined as the 100% value. The substances to be tested were pipetted as a dilution series in a duplicate determination, likewise the AUC of each substance concentration was determined and the % inhibition of the AUC against the control was calculated. By means of the % inhibition, the IC50 was calculated with the aid of a nonlinear regression analysis according to the 4 parameter equation.

Table 2 shows the results.

TABLE 2

| Compound from Example | Inhibition of platelet aggregation IC$_{50}$ [micro M] |
|---|---|
| 2 | 13 |
| 3 | 0.85 |
| 6b | 0.73 |
| 8 | 0.51 |
| 12 | 0.02 |
| 18 | 9.5 |
| 19 | 0.9 |
| 20 | 0.07 |

The invention claimed is:
1. A compound according to the formula I:

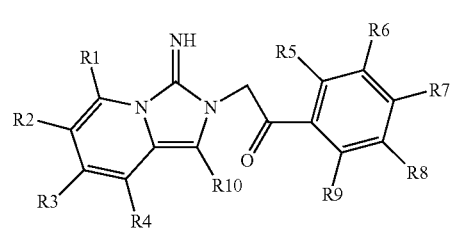

(I)

or a physiologically tolerable salt thereof, wherein:
R1, R2, R3 and R4 are identical or different and each is, independently of one another:
1) —(C$_1$-C$_6$)-alkyl, wherein said —(C$_1$-C$_6$)-alkyl is unsubstituted or mono-, di- or trisubstituted independently of one another by —(C$_6$-C$_{14}$)-aryl, —(C$_3$-C$_6$)-cycloalkyl, Het, halogen, —NH$_2$, —OH or methoxy;
2) —O—(C$_1$-C$_8$)-alkyl, wherein said —O—(C$_1$-C$_8$)-alkyl is unsubstituted or mono-, di- or trisubstituted independently of one another by —(C$_6$-C$_{14}$)-aryl, —(C$_3$-C$_6$)-cycloalkyl, Het, halogen, —NH$_2$, —OH or methoxy, wherein said —(C$_6$-C$_{14}$)-aryl and said Het are unsubstituted or additionally mono-, di- or trisubstituted by R15;
3) —(C$_0$-C$_4$)-alkylene-C(O)—R11;
4) —(C$_0$-C$_4$)-alkylene-C(O)—O—R11;
5) —(C$_0$-C$_4$)-alkylene-N(R12)-R13;
6) —(C$_0$-C$_4$)-alkylene-C(O)—N(R12)-R13;
7) —(C$_0$-C$_4$)-alkylene-N(R12)-C(O)—R13;
8) —(C$_1$-C$_3$)-fluoroalkyl;
9) —O—(C$_1$-C$_3$)-fluoroalkyl;
10) —SO$_2$—CH$_3$;
11) —SO$_2$—CF$_3$;
12) —NO$_2$;
13) —CN;
14) —OH;
15) =O;
16) a hydrogen atom; or
17) halogen;
R10 and R15 are identical or different and each is, independently of one another:
1) a hydrogen atom;
2) —(C$_1$-C$_4$)-alkyl;
3) —O—(C$_1$-C$_4$)-alkyl;
4) —(C$_1$-C$_3$)-fluoroalkyl;
5) —O—(C$_1$-C$_3$)-fluoroalkyl;
6) —(C$_0$-C$_4$)-alkylene-N(R16)(R17);
7) —(C$_0$-C$_4$)-alkylene-(C$_6$-C$_{14}$)-aryl;
8) —(C$_0$-C$_4$)-alkylene-(C$_3$-C$_6$)-cycloalkyl;
9) —(C$_0$-C$_4$)-alkylene-Het;
10) —OH;
11) =O;
12) —N$_2$;
13) —CN;
14) halogen;
15) —SO$_2$—(C$_1$-C$_4$)-alkyl; or
16) —SO$_2$—(C$_1$-C$_3$)-fluoroalkyl;
R5, R6, R7, R8 and R9 are identical or different and each is, independently of one another:
1) a hydrogen atom;
2) —(C$_0$-C$_4$)-alkylene-(C$_6$-C$_{14}$)-aryl, wherein the aryl moiety of said —(C$_0$-C$_4$)-alkylene-(C$_6$-C$_{14}$)-aryl is unsubstituted or mono-, di- or trisubstituted independently of one another by —($C_1$-$C_4$)-alkyl, —($C_6$-$C_{14}$)-aryl, Het, —($C_3$-$C_6$)-cycloalkyl, halogen, —$NH_2$, —OH or methoxy;
3) —($C_0$-$C_4$)-alkylene-($C_3$-$C_6$)-cycloalkyl;
4) —($C_0$-$C_4$)-alkylene-Het, where Het is unsubstituted or mono-, di- or trisubstituted independently of one another by —($C_1$-$C_4$)-alkyl, —($C_6$-$C_{14}$)-aryl, Het, —($C_3$-$C_6$)-cycloalkyl, —C(O)—O—R16, —C(O)—N(R16)(R17), halogen, —$NH_2$, —OH or methoxy;
5) —$SF_5$;
6) —($C_1$-$C_6$)-alkyl, wherein said —($C_1$-$C_6$)-alkyl is unsubstituted or mono-, di- or trisubstituted independently of one another by halogen, —$NH_2$, —OH or methoxy;
7) —O—($C_1$-$C_8$)-alkyl, wherein said —O—($C_1$-$C_8$)-alkyl is unsubstituted or mono-, di- or trisubstituted independently of one another by —($C_6$-$C_{14}$)-aryl, —($C_3$-$C_6$)-cycloalkyl, Het, halogen, —$NH_2$, —OH or methoxy;
8) —($C_0$-$C_4$)-alkylene-C(O)—R11;
9) —($C_0$-$C_4$)-alkylene-C(O)—O—R11;
10) —($C_0$-$C_4$)-alkylene-N(R12)-R13;
11) —($C_0$-$C_4$)-alkylene-C(O)—N(R12)—R13;
12) —($C_0$-$C_4$)-alkylene-N(R12)-C(O)—R13;
13) —($C_1$-$C_3$)-fluoroalkyl;
14) —O—($C_1$-$C_3$)-fluoroalkyl;
15) —$SO_2$—$CH_3$;
16) —$SO_2$—$CF_3$;
17) —$NO_2$;
18) —CN;
19) —OH; or
20) halogen;
or R5 and R6, R6 and R7, R7 and R8 or R8 and R9, together with the ring atoms to which they are bonded, form a four-membered to eight-membered heterocycle moiety which, together with the phenyl ring to which the heterocycle moiety is fused, forms a bicyclic system, wherein said heterocyclic moiety is unsubstituted or mono-, di- or trisubstituted independently of one another by —($C_1$-$C_4$)-alkyl, —($C_6$-$C_{14}$)-aryl, —($C_3$-$C_6$)-cycloalkyl, halogen, —$NH_2$, —OH or methoxy;
R11 is a hydrogen atom, —($C_1$-$C_6$)-alkyl, —($C_0$-$C_4$)-alkylene-($C_6$-$C_{14}$)-aryl, —($C_0$-$C_4$)-alkylene-Het, or —($C_0$-$C_4$)-alkylene-($C_3$-$C_6$)-cycloalkyl;
R12 and R13 each is, independently for each occurrence, a hydrogen atom, —($C_1$-$C_6$)-alkyl, —($C_1$-$C_3$)-fluoroalkyl, —($C_0$-$C_4$)-alkylene-($C_6$-$C_{14}$)-aryl, —($C_0$-$C_4$)-alkylene-Het or —($C_0$-$C_4$)-alkylene-($C_3$-$C_6$)-cycloalkyl; and
R16 and R17 each is, independently of one another, a hydrogen atom or —($C_1$-$C_6$)-alkyl.

2. A compound according to claim 1, wherein:
R1, R2, R3 and R4 are identical or different and each is, independently of one another:
1) —($C_1$-$C_6$)-alkyl, where alkyl is unsubstituted or mono-, di- or trisubstituted independently of one another by —($C_3$-$C_6$)-cycloalkyl, halogen, —$NH_2$, —OH, methoxy, —($C_6$-$C_{14}$)-aryl, or Het;
2) —O—($C_1$-$C_6$)-alkyl, wherein said —O—($C_1$-$C_6$)-alkyl is unsubstituted or mono-, di- or trisubstituted independently of one another by —($C_6$-$C_{14}$)-aryl, —($C_3$-$C_6$)-cycloalkyl, Het, halogen, —$NH_2$, —OH or methoxy;
3) —($C_0$-$C_4$)-alkylene-C(O)—R11;
4) —($C_0$-$C_4$)-alkylene-C(O)—O—R11;
5) —($C_0$-$C_4$)-alkylene-N(R12)—R13;
6) —($C_0$-$C_4$)-alkylene-C(O)—N(R12)—R13;
7) —($C_0$-$C_4$)-alkylene-N(R12)-C(O)—R13;
8) —($C_1$-$C_3$)-fluoroalkyl;
9) —O—($C_1$-$C_3$)-fluoroalkyl;
10) —$SO_2$—$CH_3$;
11) —$SO_2$—$CF_3$;
12) —$NO_2$;
13) —CN;
14) —OH;
15) =O;
16) a hydrogen atom; or
17) halogen;
R10 and R15 are identical or different and independently of one another are:
1) a hydrogen atom;
2) —($C_1$-$C_4$)-alkyl;
3) —O—($C_1$-$C_4$)-alkyl;
4) —($C_1$-$C_3$)-fluoroalkyl;
5) —O—($C_1$-$C_3$)-fluoroalkyl;
6) —($C_0$-$C_4$)-alkylene-N(R16)(R17);
7) —($C_0$-$C_4$)-alkylene-($C_6$-$C_{14}$)-aryl;
8) —($C_0$-$C_4$)-alkylene-($C_3$-$C_6$)-cycloalkyl;
9) —($C_0$-$C_4$)-alkylene-Het;
10) —OH;
11) =O;
12) —$NO_2$;
13) —CN;
14) halogen;
15) —$SO_2$—($C_1$-$C_4$)-alkyl; or
16) —$SO_2$—($C_1$-$C_3$)-fluoroalkyl;
R5, R6, R7, R8 and R9 are identical or different and independently of one another are
1) a hydrogen atom;
2) —($C_0$-$C_4$)-alkylene-($C_6$-$C_{14}$)-aryl, where aryl is unsubstituted or mono-, di- or trisubstituted independently of one another by —($C_1$-$C_4$)-alkyl, —($C_6$-$C_{14}$)-aryl, Het, —($C_3$-$C_6$)-cycloalkyl, halogen, —$NH_2$, —OH or methoxy;
3) —($C_0$-$C_4$)-alkylene-($C_3$-$C_6$)-cycloalkyl;
4) —($C_0$-$C_4$)-alkylene-Het, where Het is unsubstituted or mono-, di- or trisubstituted independently of one another by —($C_1$-$C_4$)-alkyl, —($C_6$-$C_{14}$)-aryl, Het, —($C_3$-$C_6$)-cycloalkyl, —C(O)—O—R16, —C(O)—N(R16)(R17), halogen, —$NH_2$, —OH or methoxy;
5) —$SF_5$;
6) —($C_1$-$C_6$)-alkyl, where alkyl is unsubstituted or mono-, di- or trisubstituted independently of one another by halogen, —$NH_2$, —OH or methoxy;
7) —O—($C_1$-$C_8$)-alkyl, where alkyl is unsubstituted or mono-, di- or trisubstituted independently of one another by —($C_6$-$C_{14}$)-aryl, —($C_3$-$C_6$)-cycloalkyl, Het, halogen, —$NH_2$, —OH or methoxy;
8) —($C_0$-$C_4$)-alkylene-C(O)—R11;
9) —($C_0$-$C_4$)-alkylene-C(O)—O—R11;
10) —($C_0$-$C_4$)-alkylene-N(R12)—R13;
11) —($C_0$-$C_4$)-alkylene-C(O)—N(R12)-R13;
12) —($C_0$-$C_4$)-alkylene-N(R12)—C(O)—R13;
13) —($C_1$-$C_3$)-fluoroalkyl;
14) —O—($C_1$-$C_3$)-fluoroalkyl;
15) —$SO_2$—$CH_3$;
16) —$SO_2$—$CF_3$;
17) —$NO_2$;
18) —CN;
19) —OH; or
20) halogen;
or R5 and R6, R6 and R7, R7 and R8 or R8 and R9, together with the ring atoms to which they are bonded, form a four- to eight-membered heterocycle which, together with the phenyl ring to which the heterocycle is fused, forms a bicyclic system selected from the group consisting of benzimidazole, benzisothiazole, benzisoxazole, benzo[1,3]dioxole, benzofuranyl, benzothiazole, benzisoxazole, benzothiofuran, benzothiophene, benzo[1,3]oxathiole, benzoxazole, benzothiazole, benzotriazolyl, quinazoline, quinazolone, quinoline, 4H-quinolizine, quinoxaline, chroman, chromene, cinnoline, 2,3-dihydrobenzo[1,4]dioxin, 2,3-dihydrobenzofuranyl, 1,3-dihydro-isobenzofuran, 3,4-dihydro-2H-benzo[1,4]oxazine, 2,3-dihydrobenzooxazole, 2,3-dihydrobenzothiazole, 1,3-dihydrobenzo[c]thiophene, 2,3-dihydro-benzo[b]thiophene, indazole, indole, indoline, isobenzofuran, isoquinoline, isochroman, isoindazole, isoindole, isoindoline, 7-oxabicyclo[4.2.0]octa-1,3,5-triene, phthalazine, 2,3,4,5-tetrahydro-1H-benzo[b]azepine, 6,7,8,9-tetrahydro-5-oxa-9-azabenzocycloheptene, 3,4,5,6-tetrahydro-2H-benzo[b][1,4]oxazozine, tetrahydroquinoline, 1,2,3,4-tetrahydroquinoxaline or tetrahydroisoquinoline, where the heterocyclic moiety is unsubstituted or mono-, di- or trisubstituted independently of one another by —($C_1$-$C_4$)-alkyl, —($C_6$-$C_{14}$)-aryl, —($C_3$-$C_6$)-cycloalkyl, halogen, —$NH_2$, —OH or methoxy;

and wherein:

said —($C_6$-$C_{14}$)-aryl is, independently for each occurrence, selected from the group consisting of phenyl, naphthyl, anthryl and fluorenyl, in which said phenyl, naphthyl, anthryl and fluorenyl is unsubstituted or mono-, di- or trisubstituted by R15;

said Het is, independently for each occurrence, selected from the group consisting of acridinyl, azepinyl, azetidinyl, aziridinyl, benzimidazolyl, benzofuranyl, benzothiofuranyl, benzothiophenyl, benzoxazolyl, benzothiazolyl, benzotriazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]tetrahydrofuranyl, dihydrofuranyl, dioxolyl, dioxanyl, 2H,6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolidinyl, thiazolinyl, thiazolyl, thienyl, thienoimidazolyl, thienooxazolyl, thienopyrrolyl, thienopyridinyl, thienothiazolyl, thienothiophenyl, thiomorpholinyl, triazinyl, 1,2,3-triazolyl, 1,2,4-triazolyl, 1,2,5-triazolyl, 1,3,4-triazolyl and xanthenyl and in which Het is unsubstituted or additionally mono-, di- or trisubstituted by R15;

said R11 is, independently for each occurrence, a hydrogen atom, —(C1-C6)-alkyl, —(C0-C4)-alkylene-(C6-C14)-aryl, —(C0-C4)-alkylene-Het, or —(C0-C4)-alkylene-(C3-C6)-cycloalkyl;

said R12 and R13 each is, independently for each occurrence, a hydrogen atom, —(C1-C6)-alkyl —(C1-C3)-fluoroalkyl, —(C0-C4)-alkylene-(C6-C14)-aryl, —(C0-C4)-alkylene-Het, or —(C0-C4)-alkylene-(C3-C6)-cycloalkyl; and said R16 and R17 each is, independently for each occurrence, a hydrogen atom or —($C_1$-$C_6$)-alkyl;

or a physiologically tolerable salt thereof.

3. A compound according to claim 2, wherein:

R1, R2, R3 and R4 are identical or different and each is, independently of one another:
1) a hydrogen atom;
2) —($C_1$-$C_4$)-alkyl;
3) —O—($C_1$-$C_4$)-alkyl;
4) —($C_0$-$C_4$)-alkylene-C(O)—N(R12)—R13, where R12 and R13 are identical or different and independently of one another are a hydrogen atom or —($C_1$-$C_4$)-alkyl;
5) —($C_1$-$C_3$)-fluoroalkyl;
6) —($C_0$-$C_4$)-alkylene-C(O)—O—($C_1$-$C_4$)-alkyl;
7) =O; or
8) halogen;

R10 is:
1) a hydrogen atom;
2) —($C_1$-$C_4$)-alkyl;
3) —($C_0$-$C_4$)-alkylene-($C_3$-$C_6$)-cycloalkyl; or
4) —($C_0$-$C_4$)-alkylenephenyl;

R5, R6, R7, R8 and R9 are identical or different and each is, independently of one another:
1) a hydrogen atom;
2) —($C_1$-$C_3$)-fluoroalkyl;
3) halogen;
4) —O—($C_1$-$C_4$)-alkyl;
5) —OH;
6) —($C_1$-$C_4$)-alkyl;
7) —$SF_5$;
8) —($C_0$-$C_4$)-alkylene-NH—C(O)—($C_1$-$C_3$)-fluoroalkyl;
9) —($C_0$-$C_4$)-alkylene-N(R12)—R13, where R12 and R13 are identical or different and independently of one another are a hydrogen atom or —($C_1$-$C_4$)-alkyl; or
10) —($C_0$-$C_4$)-alkylene-Het, where Het is selected from the group consisting of morpholinyl or pyrrolidinyl and is unsubstituted or mono- or disubstituted independently of one another by —($C_1$-$C_4$)-alkyl, =O or —$NH_2$;

or R5 and R6, R6 and R7, R7 and R8 or R8 and R9, together with the ring atoms to which they are bonded, form a four- to eight-membered heterocycle which, together with the phenyl ring to which the heterocycle is fused, forms a bicyclic system selected from the group consisting of 2,3-dihydro-benzo[1,4]dioxin, benzo[1,3]dioxole, 3,4-dihydro-2H-benzo[1,4]oxazine, 2,3,4,5-tetrahydro-1H-benzo[b]azepine, tetrahydroquinoline, tetrahydroisoquinoline, 1,2,3,4-tetrahydroquinoxaline or 6,7,8,9-tetrahydro-5-oxa-9-azabenzocycloheptene, where the heterocyclic moiety is unsubstituted or mono- or disubstituted by —($C_1$-$C_4$)-alkyl or halogen;

or a physiologically tolerable salt thereof.

4. A compound according to claim 1, wherein said compound is:

1-(3,5-di-tert-butyl-4-hydroxyphenyl)-2-(3-iminoimidazo[1,5-a]pyridin-2-yl)ethanone;

2-(3-iminoimidazo[1,5-a]pyridin-2-yl)-1-(3-pentafluorosulfanylphenyl)ethanone;

2-(1-cyclopropyl-3-iminoimidazo[1,5-a]pyridin-2-yl)-1-(3,5-di-tert-butyl-4-hydroxyphenyl)ethanone;

1-(3,5-di-tert-butyl-4-hydroxyphenyl)-2-(3-imino-1-phenylimidazo[1,5-a]pyridin-2-yl)ethanone;

1-(3,5-di-tert-butyl-4-hydroxyphenyl)-2-(3-imino-8-methylimidazo[1,5-a]pyridin-2-yl)ethanone;

1-(3,5-di-tert-butyl-4-hydroxyphenyl)-2-(3-imino-7-trifluoromethylimidazo[1,5-a]pyridin-2-yl)ethanone;

methyl 2-[2-(3,5-di-tert-butyl-4-hydroxyphenyl)-2-oxoethyl]-3-imino-2,3-dihydroimidazo[1,5-a]pyridine-6-carboxylate;

methyl 2-[2-(3-tert-butyl-4-methoxy-5-morpholin-4-ylphenyl)-2-oxoethyl]-3-imino-2,3-dihydroimidazo[1,5-a]pyridine-6-carboxylate;

1-(3-tert-butyl-4-methoxy-5-morpholin-4-ylphenyl)-2-(3-iminoimidazo[1,5-a]pyridin-2-yl)ethanone;

1-(3-tert-butyl-4-methoxy-5-morpholin-4-ylphenyl)-2-(3-imino-8-methylimidazo[1,5-a]pyridin-2-yl)ethanone;

1-(3-dimethylamino-5-pentafluorosulfanylphenyl)-2-(3-iminoimidazo[1,5-a]pyridin-2-yl)ethanone;

2-[2-(8-tert-butyl-4-methyl-3,4-dihydro-2H-benzo[1,4]oxazin-6-yl)-2-oxoethyl]-7-ethoxy-3-imino-2,3-dihydroimidazo[1,5-a]pyridine-6-carboxylic acid methylamide;

2-[2-(3-tert-butyl-4-methoxy-5-morpholin-4-ylphenyl)-2-oxoethyl]-7-chloro-3-imino-2,3-dihydroimidazo[1,5-a]pyridine-6-carboxylic acid methylamide;

2,2,2-trifluoro-N-{3-[2-(3-iminoimidazo[1,5-a]pyridin-2-yl)acetyl]-5-pentafluorosulfanylphenyl}acetamide;

1-(3-bromo-4-methoxy-5-trifluoromethylphenyl)-2-(3-iminoimidazo[1,5-a]pyridin-2-yl)ethanone;

2-(3-iminoimidazo[1,5-a]pyridin-2-yl)-1-(4-methoxy-3-morpholin-4-yl-5-trifluoromethylphenyl)ethanone;

6-ethoxy-3-imino-2-[2-(3-methylamino-5-pentafluorosulfanylphenyl)-2-oxoethyl]-2,3-dihydro-1H-imidazo[1,5-a]pyridin-5-one;

2-[2-(3-tert-butyl-4-methoxy-5-morpholin-4-ylphenyl)-2-oxoethyl]-6-ethoxy-3-imino-2,3-dihydro-1H-imidazo[1,5-a]pyridin-5-one;

2-[2-(3-tert-butyl-4-methoxy-5-morpholin-4-ylphenyl)-2-oxoethyl]-7-ethoxy-3-imino-2,3-dihydroimidazo[1,5-a]pyridine-6-carboxylic acid methylamide; or ethyl 2-[2-(3-tert-butyl-4-methoxy-5-morpholin-4-ylphenyl)-2-oxoethyl]-3-imino-5-methoxy-2,3-dihydroimidazo[1,5-a]pyridine-7-carboxylate;

or a physiologically tolerable salt thereof.

5. A compound according to claim 4, wherein said compound is:

1-(3,5-di-tert-butyl-4-hydroxyphenyl)-2-(3-imino-8-methylimidazo[1,5-a]pyridin-2-yl)ethanone as the hydrobromide salt;

1-(3,5-di-tert-butyl-4-hydroxyphenyl)-2-(3-imino-7-trifluoromethylimidazo[1,5-a]pyridin-2-yl)ethanone as the hydrobromide salt;

2,2,2-trifluoro-N-{3-[2-(3-iminoimidazo[1,5-a]pyridin-2-yl)acetyl]-5-pentafluorosulfanylphenyl}acetamide ;

1-(3-bromo-4-methoxy-5-trifluoromethylphenyl)-2-(3-iminoimidazo[1,5-a]pyridin-2-yl)ethanone ;

2-(3-iminoimidazo[1,5-a]pyridin-2-yl)-1-(4-methoxy-3-morpholin-4-yl-5-trifluoromethylphenyl)ethanone ;

6-ethoxy-3-imino-2-[2-(3-methylamino-5-pentafluorosulfanylphenyl)-2-oxoethyl]-2,3-dihydro-1H-imidazo[1,5-a]pyridin-5-one ;

2-[2-(3-tert-butyl-4-methoxy-5-morpholin-4-ylphenyl)-2-oxoethyl]-6-ethoxy-3-imino-2,3-dihydro-1H-imidazo[1,5-a]pyridin-5-one ;

2-[2-(3-tert-butyl-4-methoxy-5-morpholin-4-ylphenyl)-2-oxoethyl]-7-ethoxy-3-imino-2,3-dihydroimidazo[1,5-a]pyridine-6-carboxylic acid methylamide ; or ethyl 2-[2-(3-tert-butyl-4-methoxy-5-morpholin-4-ylphenyl)-2-oxoethyl]-3-imino-5-methoxy-2,3-dihydroimidazo[1,5-a]pyridine-7-carboxylate .

6. A pharmaccutical composition which comprises an efficacious amount of at least one compound according to claim 1 together with a pharmaceutically suitable and physiologically tolerable vehicle, additive and/or other active ingredients and excipients.

7. A process for the preparation of a compound according to claim 1, which comprises:

a) reacting a compound of the formula II:

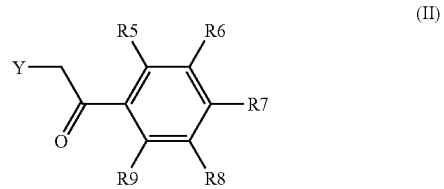

wherein Y is chloride, bromide, mesylate or tosylate, with a compound of the formula III:

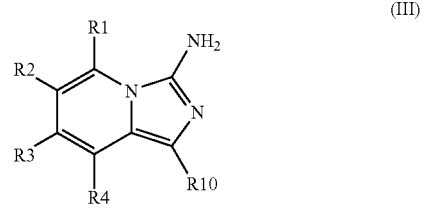

in the presence of a base and of a solvent to give a compound of the formula I; or b) reacting a compound of the formula VII:

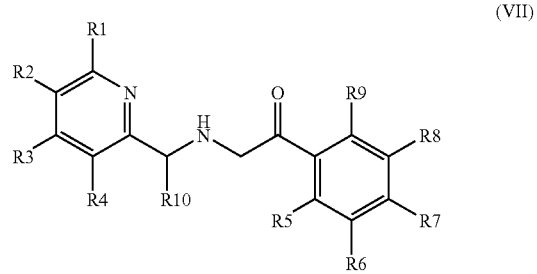

with a compound Z—CN, where Z is tosylate or bromide, in the presence of a base to give a compound of the formula I; or c) either isolating the compound of the formula I prepared according to process a) or b) in free form or releasing it from physiologically intolerable salts or, in the case of the presence of acidic or basic groups, converting it to physiologically tolerable salts; or d) separating a compound of the formula I prepared according to process a) or b), or a suitable precursor of the formula I, which on account of its chemical structure occurs in enantiomeric or diastereomeric forms, by salt formation with enantiomerically pure acids or bases, chromatography on chiral stationary phases or derivatization by means of chiral enantiomerically pure compounds such as amino acids, separation of the diastereomers thus obtained, and cleavage of the chiral auxiliary groups into the pure enantiomers or diastereomers.

8. A process for the preparation of a compound of the formula VII according to claim 7,

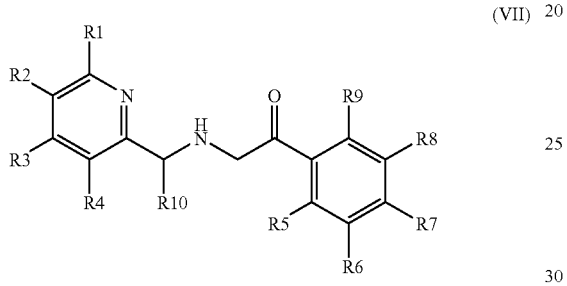
(VII)

said process comprising reacting a compound of the formula VIII:

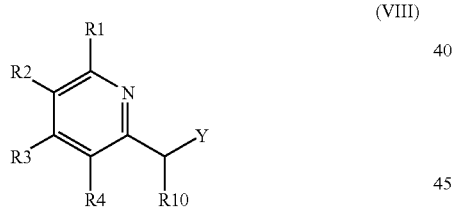
(VIII)

wherein Y is chloride, bromide, mesylate or tosylate, with a compound of the formula IX:

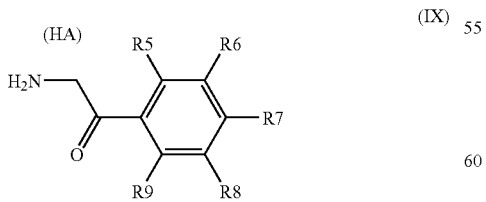
(IIA) (IX)

in the presence of a base and of a solvent to give a compound of the formula VII.

9. A process for the preparation of a compound of the formula II according to claim 7,

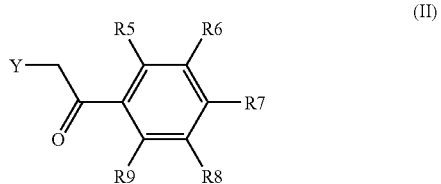
(II)

wherein Y is Br, and one of the radicals R5, R6, R7, R8 or R9 is pentafluorosulfanyl, said process comprising:

a) converting a compound of the formula Xa:

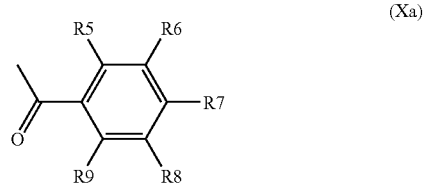
(Xa)

where one of the radicals R5, R6, R7, R8 or R9 is pentafluorosulfanyl, with a brominating reagent to the compound of the formula II; or b) treating a compound of the formula XIa:

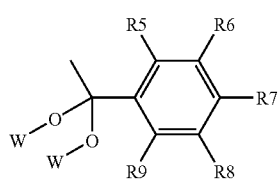

where one of the radicals R5, R6, R7, R8 or R9 is pentafluorosulfanyl, W is ethylene, propylene or butylene or, together with the group —O—C—O—, forms a 1,3-dioxo ring of ring size 5, 6 or 7, with a brominating reagent and subsequently converted in the presence of an acid to the compound of the formula II.

10. A process for the preparation of a compound of the formula Xa according to claim 9:

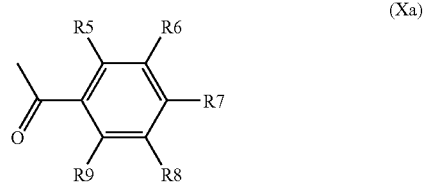
(Xa)

wherein R6 is pentafluorosulfanyl and R8 is dimethylamine, a) said process comprises the step of first nitrating a compound of the formula XIVa:

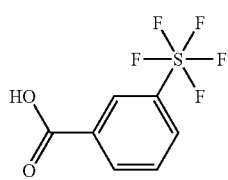

(XIVa)

and subsequently reducing said compound with hydrogen to give the amine of the formula XIIIa:

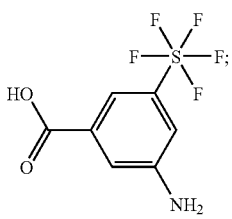

(XIIIa)

b) dimethylating the compound of the formula XIIIa on the nitrogen, converting the carboxylic acid with thionyl chloride to the acid chloride, reacting the resulting compound with O,N-dimethylhydroxylamine to give a compound of the formula XIIa:

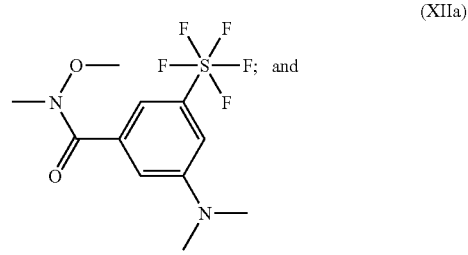

(XIIa)

c) converting the compound of the formula XIIa with methylmagnesium bromide to the compound of the formula Xa.

\* \* \* \* \*

UNITED STATES PATENT AND TRADEMARK OFFICE
CERTIFICATE OF CORRECTION

PATENT NO.        : 7,863,269 B2
APPLICATION NO.   : 12/364124
DATED             : January 4, 2011
INVENTOR(S)       : Uwe Heinelt et al.

It is certified that error appears in the above-identified patent and that said Letters Patent is hereby corrected as shown below:

In column 7, line 25, delete "oxazozine," and insert -- oxazoline, --, therefor.

In column 10, line 46, delete "oxazozine," and insert -- oxazoline, --, therefor.

In column 58, line 57, in claim 1, delete " —$N_2$;" and insert -- —$NO_2$; --, therefor.

In column 61, line 17, in claim 2, delete "oxazozine," and insert -- oxazoline, --, therefor.

In column 63, line 63, in claim 5, after "acetamide" insert -- as the trifluoroacetic acid salt --.

In column 63, line 65, in claim 5, after "ethanone" insert -- as the trifluoroacetic acid salt --.

In column 63, line 67, in claim 5, after "ethanone" insert -- as the trifluoroacetic acid salt --.

In column 64, line 3, in claim 5, after "one" insert -- as the trifluoroacetic acid salt --.

In column 64, line 6, in claim 5, after "one" insert -- as the trifluoroacetic acid salt --.

In column 64, line 9, in claim 5, after "methylamide" insert -- as the trifluoroacetic acid salt --.

In column 64, line 12, in claim 5, after "carboxylate" insert -- as the trifluoroacetic acid salt --.

Signed and Sealed this
Eleventh Day of October, 2011

David J. Kappos
*Director of the United States Patent and Trademark Office*